(12) United States Patent
Brzeczko et al.

(10) Patent No.: US 11,554,114 B2
(45) Date of Patent: Jan. 17, 2023

(54) METHODS AND COMPOSITIONS FOR SELF-REGULATED RELEASE OF ACTIVE PHARMACEUTICAL INGREDIENTS

(71) Applicant: ACURA PHARMACEUTICALS, INC., Palatine, IL (US)

(72) Inventors: Albert W. Brzeczko, Rosswell, GA (US); Robert Barnett Jones, Summit, NJ (US)

(73) Assignee: Acura Pharmaceuticals, Inc., Palatine, IL (US)

( * ) Notice: Subject to any disclaimer, the term of this patent is extended or adjusted under 35 U.S.C. 154(b) by 0 days.

(21) Appl. No.: 16/498,746

(22) PCT Filed: Mar. 30, 2018

(86) PCT No.: PCT/US2018/025449
§ 371 (c)(1),
(2) Date: Sep. 27, 2019

(87) PCT Pub. No.: WO2018/183881
PCT Pub. Date: Oct. 4, 2018

(65) Prior Publication Data
US 2021/0113542 A1    Apr. 22, 2021

Related U.S. Application Data

(60) Provisional application No. 62/479,822, filed on Mar. 31, 2017, provisional application No. 62/544,375, filed on Aug. 11, 2017, provisional application No. 62/587,783, filed on Nov. 17, 2017.

(51) Int. Cl.

| | |
|---|---|
| *A61K 31/451* | (2006.01) |
| *A61K 9/16* | (2006.01) |
| *A61K 31/426* | (2006.01) |
| *A61K 31/46* | (2006.01) |
| *A61K 31/485* | (2006.01) |
| *A61K 45/06* | (2006.01) |
| *A61K 47/02* | (2006.01) |
| *A61K 47/12* | (2006.01) |
| *A61K 47/14* | (2017.01) |
| *A61K 47/26* | (2006.01) |
| *A61K 47/32* | (2006.01) |
| *A61K 47/36* | (2006.01) |
| *A61K 47/38* | (2006.01) |
| *A61K 47/42* | (2017.01) |
| *A61K 47/46* | (2006.01) |

(52) U.S. Cl.
CPC ............ *A61K 31/451* (2013.01); *A61K 9/167* (2013.01); *A61K 9/1611* (2013.01); *A61K 9/1617* (2013.01); *A61K 9/1635* (2013.01); *A61K 9/1652* (2013.01); *A61K 9/1694* (2013.01); *A61K 31/426* (2013.01); *A61K 31/46* (2013.01); *A61K 31/485* (2013.01); *A61K 45/06* (2013.01); *A61K 47/02* (2013.01); *A61K 47/12* (2013.01); *A61K 47/14* (2013.01); *A61K 47/26* (2013.01); *A61K 47/32* (2013.01); *A61K 47/36* (2013.01); *A61K 47/38* (2013.01); *A61K 47/42* (2013.01); *A61K 47/46* (2013.01)

(58) Field of Classification Search
CPC .... A61K 9/1611; A61K 47/38; A61K 31/451; A61K 9/5078; A61K 45/06; A61K 47/26; A61K 47/32; A61K 9/1617; A61K 9/1652; A61K 9/167; A61K 31/426; A61K 47/42; A61K 9/2077; A61K 47/46; A61K 31/485; A61K 47/12; A61K 9/1694; A61K 9/1635; A61K 31/46; A61K 47/02; A61K 47/36; A61K 47/14; A61K 2300/00; A61K 9/5026; A61P 25/36
See application file for complete search history.

(56) References Cited

U.S. PATENT DOCUMENTS

| | | | | |
|---|---|---|---|---|
| 4,786,505 | A * | 11/1988 | Lovgren | A61K 9/5073 424/468 |
| 2013/0017263 | A1* | 1/2013 | Pettersson | A61P 31/04 424/484 |
| 2015/0272902 | A1* | 10/2015 | Dharmadhikari | A61P 25/24 424/487 |
| 2016/0346274 | A1* | 12/2016 | Vaka | A61K 9/501 |
| 2017/0056501 | A1 | 3/2017 | Jones | |

FOREIGN PATENT DOCUMENTS

| | | | | |
|---|---|---|---|---|
| WO | 2015145459 A1 | 10/2015 | | |
| WO | 2016023108 A1 | 2/2016 | | |
| WO | WO-2016120892 A1 * | 8/2016 | ........... | A61K 9/2077 |
| WO | 2018/183881 | 10/2018 | | |

OTHER PUBLICATIONS

European Search Report for corresponding Application No. 18 776 335.4 dated Nov. 6, 2020, 6 pages.
Office Action for corresponding application JP2019-553509 dated Oct. 23, 2020, 10 pages.
International Search Report for International Application No. PCT/US2018/025449 dated Jun. 21, 2018, 3 pages.
Written Opinion for International Application No. PCT/US2018/025449 dated Jun. 21, 2018, 4 pages.
Examination Report for corresponding Australian Patent Application No. 2018243657 dated Sep. 4, 2020, 5 pages.
Office Action dated Jul. 7, 2021 for corresponding Australian application No. 2018243657 (4 pages).
Notice of Reasons for Rejection for corresponding JP Application No. 2019-553509 dated Jun. 24, 2021, 4 pages.
Notice of Reasons for Refusal dated Feb. 14, 2022, of counterpart Japanese Patent Application No. 2019-553509, along with an English translation.

(Continued)

*Primary Examiner* — Doan T Phan
(74) *Attorney, Agent, or Firm* — DLA Piper LLP (US)

(57) ABSTRACT

An abuse deterrent pharmaceutical composition including a drug susceptible to abuse, a first acid soluble ingredient, a first buffering ingredient, and a delayed release buffering component.

18 Claims, 1 Drawing Sheet

(56) References Cited

OTHER PUBLICATIONS

A.L.R. Rattes et al., "Spray -Diying as a Method for Microparticulate Modified Release Systems Preparation," Drying 2004—Proceedings of the 14$^{th}$ International Drying Symposium, vol. B, pp. 1112-1119, Aug. 2004, in English.
D.L. Costill et al., "Factors Limiting Gastric Emptying during Rest and Exercise," Journal of Applied Physiology, vol. 37, No. 5, pp. 679-683, 1998, in English.
H. Naito et al., "Regulatory Mechanisms of Gastric Emptying," Journal of Japanese Society of Gastroenterology, vol. 95, No. 12, pp. 1317-1326, 1998, English Abstract only.
Notice of Reasons for Rejection dated Aug. 1, 2022, of counterpart Japanese Patent Application No. 2019-553509, along with an English translation.

* cited by examiner

METHODS AND COMPOSITIONS FOR SELF-REGULATED RELEASE OF ACTIVE PHARMACEUTICAL INGREDIENTS

CROSS-REFERENCE TO RELATED APPLICATIONS

This application is a U.S. National Stage application of International Patent Application No. PCT/US2018/025449 filed Mar. 30, 2018, which claims the benefit of U.S. Provisional Patent Application Nos. 62/479,822 filed Mar. 31, 2017, 62/544,375 filed Aug. 11, 2017, and 62/587,783 filed Nov. 17, 2017, all of which are incorporated by reference herein in their entireties.

BACKGROUND OF THE INVENTION

The class of drugs exhibiting opium or morphine-like properties are referred to as opioids, or opioid agonists. As agonists, certain drugs are characterized as interacting with stereo specific and saturable binding sites in the brain and other body tissues and organs. Endogenous opioid-like peptides are present in areas of the central nervous system that are presumed to be related to the perception of pain, to movement, mood and behavior, and to the regulation of neuroendocrinological functions. Three classical opioid receptor types, mu ($\mu$), delta ($\delta$), and kappa ($\kappa$), have been studied extensively. Each of these receptors has a unique anatomical distribution in the brain, spinal cord, and the periphery. Most of the clinically used opioids are relatively selective for $\mu$ receptors, reflecting their similarity to morphine. However, opioid containing drugs that are relatively selective for a particular receptor subtype at standard therapeutic doses will often interact with multiple receptor subtypes when given at sufficiently high doses, leading to possible changes in their pharmacological effect. This is especially true as opioid doses are escalated to overcome tolerance.

Repeated opioid use leads to potential development of tolerance, physical, and/or psychological dependence, i.e., addiction, which is a characteristic feature of most drugs containing opioid analgesics.

Attempts have been made to diminish the abuse potential of orally administered drugs, including opioids. These attempts generally centered on the inclusion in the oral dosage form of an opioid antagonist which is not orally active but which will substantially block the analgesic effects of the opioid if one attempts to dissolve the opioid and administer it parenterally.

Despite all attempts however, the misuse and abuse of pharmaceutical products continues to increase. There is a growing need for novel and effective methods and compositions to deter abuse of pharmaceutical products (e.g., orally administered pharmaceutical products), including but not limited to immediate release, sustained or extended release and delayed release formulations for drugs subject to abuse. In particular, such methods and compositions would be useful for opioid analgesics, for patients seeking drug therapy, which deter abuse and minimize or reduce the potential for physical or psychological dependency.

SUMMARY OF THE INVENTION

In one embodiment, the invention relates to an abuse deterrent pharmaceutical composition including a drug susceptible to abuse; a first acid soluble ingredient; a first buffering ingredient; and a delayed release buffering component. In some embodiments, the first acid soluble ingredient includes calcium carbonate, a cationic copolymer, or a combination thereof. In some embodiments, the cationic copolymer includes one or more of dimethylaminoethyl methacrylate, butyl methacrylate, and methyl methacrylate. In some embodiments, the first buffering ingredient includes calcium carbonate, sodium bicarbonate, magnesium oxide, tribasic sodium phosphate, or combinations thereof. In some embodiments, the delayed release buffering component comprises a second buffering ingredient, an enteric agent, and a sustained-release ingredient. In some embodiments, the delayed release buffering component comprises a core, a shell surrounding the core, and a subcoat between the core and the shell, wherein the core comprises the second buffering ingredient, the shell comprises the enteric agent, and the subcoat comprises the sustained-release ingredient. In some embodiments, the delayed release buffering component comprises a second buffering ingredient, an enteric agent, and a second acid-soluble ingredient. In some embodiments, the delayed release buffering component comprises a core, a shell surrounding the core, and a subcoat between the core and the shell, wherein the core comprises the second buffering ingredient, the shell comprises the enteric agent, and the subcoat comprises the second acid-soluble ingredient. In some embodiments, the second acid soluble ingredient comprises calcium carbonate, a cationic copolymer, or combinations thereof. In some embodiments, the cationic copolymer comprises one or more of dimethylaminoethyl methacrylate, butyl methacrylate, and methyl methacrylate. In some embodiments, the second acid soluble ingredient is the same as the first acid soluble ingredient. In some embodiments, the second buffering ingredient comprises calcium carbonate, sodium bicarbonate, magnesium oxide, tribasic sodium phosphate, or combinations thereof. In some embodiments, the second buffering ingredient is the same as the first buffering ingredient. In some embodiments, the enteric ingredient comprises one or more of shellac, methyl acrylate-methacrylic acid copolymers, cellulose acetate phthalate, cellulose acetate succinate, hydroxypropyl methyl cellulose phthalate, hypromellose acetate succinate, polyvinyl acetate phthalate, sodium alginate, and zein.

In one embodiment, the invention relates to an abuse deterrent pharmaceutical composition including a drug susceptible to abuse; a first acid soluble ingredient; a first buffering ingredient; a delayed release buffering component; and an ingredient for decreasing gastric acid production. In some embodiments, the ingredient for decreasing gastric acid production comprises an H2-antagonist. In some embodiments, the H2-antagonist is present in an amount that is 10-50% of the lowest therapeutic dose of the H2 antagonist for reducing stomach acid secretion. In some embodiments, the first acid soluble ingredient includes calcium carbonate, a cationic copolymer, or a combination thereof. In some embodiments, the cationic copolymer includes one or more of dimethylaminoethyl methacrylate, butyl methacrylate, and methyl methacrylate. In some embodiments, the first buffering ingredient includes calcium carbonate, sodium bicarbonate, magnesium oxide, tribasic sodium phosphate, or combinations thereof. In some embodiments, the delayed release buffering component comprises a second buffering ingredient, an enteric agent, and a sustained-release ingredient. In some embodiments, the delayed release buffering component comprises a core, a shell surrounding the core, and a subcoat between the core and the shell, wherein the core comprises the second buffering ingredient, the shell comprises the enteric agent, and the subcoat comprises the sustained-release ingredient. In some embodiments, the delayed release buffering component comprises a second buffering ingredient, an enteric agent, and a second acid-soluble ingredient. In some embodiments, the delayed release buffering component comprises a core, a shell surrounding the core, and a subcoat between the core and the shell, wherein the core comprises the second buffering ingredient, the shell comprises the enteric agent, and the subcoat comprises the second acid-soluble ingredient. In some embodiments, the second acid soluble ingredient comprises calcium carbonate, a cationic copolymer, or combinations thereof. In some embodiments, the cationic copolymer comprises one or more of dimethylaminoethyl methacrylate, butyl methacrylate, and methyl methacrylate. In some embodiments, the second acid soluble ingredient is the same as the first acid soluble ingredient. In some embodiments, the second buffering ingredient comprises calcium carbonate, sodium bicarbonate, magnesium oxide, tribasic sodium phosphate, or combinations thereof. In some embodiments, the second buffering ingredient is the same as the first buffering ingredient. In some embodiments, the enteric ingredient comprises one or more of shellac, methyl acrylate-methacrylic acid copolymers, cellulose acetate phthalate, cellulose acetate succinate, hydroxypropyl methyl cellulose phthalate, hypromellose acetate succinate, polyvinyl acetate phthalate, sodium alginate, and zein.

In one embodiment, the invention relates to an abuse deterrent pharmaceutical composition including a drug susceptible to abuse; a first acid soluble ingredient; a first buffering ingredient; a delayed release buffering component; and an ingredient for increasing gastric emptying time. In some embodiments, the ingredient for increasing gastric emptying time is selected from the group consisting of a monosaccharide, a disaccharide, an oligosaccharide, a polysaccharide, an amino acid, a peptide, a protein, a fatty acid, a monoglyceride, a diglyceride, and a triglyceride. In some embodiments, the ingredient for increasing gastric emptying time is selected from the group consisting of loperamide, diphenoxylate, atropine, difenoxin, an anticholinergic, an antidepressant, an opioid, an antidiarrheal drug, and a gastroparesis inducing drug. In some embodiments, upon ingestion by a subject, the ingredient for increasing gastric emptying time increases the gastric emptying time of the subject. In some embodiments, the first acid soluble ingredient includes calcium carbonate, a cationic copolymer, or a combination thereof. In some embodiments, the cationic copolymer includes one or more of dimethylaminoethyl methacrylate, butyl methacrylate, and methyl methacrylate. In some embodiments, the first buffering ingredient includes calcium carbonate, sodium bicarbonate, magnesium oxide, tribasic sodium phosphate, or combinations thereof. In some embodiments, the delayed release buffering component comprises a second buffering ingredient, an enteric agent, and a sustained-release ingredient. In some embodiments, the delayed release buffering component comprises a core, a shell surrounding the core, and a subcoat between the core and the shell, wherein the core comprises the second buffering ingredient, the shell comprises the enteric agent, and the subcoat comprises the sustained-release ingredient. In some embodiments, the delayed release buffering component comprises a second buffering ingredient, an enteric agent, and a second acid-soluble ingredient. In some embodiments, the delayed release buffering component comprises a core, a shell surrounding the core, and a subcoat between the core and the shell, wherein the core comprises the second buffering ingredient, the shell comprises the enteric agent, and the subcoat comprises the second acid-soluble ingredient. In some embodiments, the second acid soluble ingredient comprises calcium carbonate, a cationic copolymer, or combinations thereof. In some embodiments, the cationic copolymer comprises one or more of dimethylaminoethyl methacrylate, butyl methacrylate, and methyl methacrylate. In some embodiments, the second acid soluble ingredient is the same as the first acid soluble ingredient. In some embodiments, the second buffering ingredient comprises calcium carbonate, sodium bicarbonate, magnesium oxide, tribasic sodium phosphate, or combinations thereof. In some embodiments, the second buffering ingredient is the same as the first buffering ingredient. In some embodiments, the enteric ingredient comprises one or more of shellac, methyl acrylate-methacrylic acid copolymers, cellulose acetate phthalate, cellulose acetate succinate, hydroxypropyl methyl cellulose phthalate, hypromellose acetate succinate, polyvinyl acetate phthalate, sodium alginate, and zein.

In one embodiment, the invention relates to an abuse deterrent pharmaceutical composition including a drug susceptible to abuse; a first acid soluble ingredient; a first buffering ingredient; a delayed release buffering component; an ingredient for decreasing gastric acid production; and an ingredient for increasing gastric emptying time. In some embodiments, the ingredient for increasing gastric emptying time is selected from the group consisting of a monosaccharide, a disaccharide, an oligosaccharide, a polysaccharide, an amino acid, a peptide, a protein, a fatty acid, a monoglyceride, a diglyceride, and a triglyceride. In some embodiments, the ingredient for increasing gastric emptying time is selected from the group consisting of loperamide, diphenoxylate, atropine, difenoxin, an anticholinergic, an antidepressant, an opioid, an antidiarrheal drug, and a gastroparesis inducing drug. In some embodiments, upon ingestion by a subject, the ingredient for increasing gastric emptying time increases the gastric emptying time of the subject. In some embodiments, the ingredient for decreasing gastric acid production comprises an H2-antagonist. In some embodiments, the H2-antagonist is present in an amount that is 10-50% of the lowest therapeutic dose of the H2 antagonist for reducing stomach acid secretion. In some embodiments, the first acid soluble ingredient includes calcium carbonate, a cationic copolymer, or a combination thereof. In some embodiments, the cationic copolymer includes one or more of dimethylaminoethyl methacrylate, butyl methacrylate, and methyl methacrylate. In some embodiments, the first buffering ingredient includes calcium carbonate, sodium bicarbonate, magnesium oxide, tribasic sodium phosphate, or combinations thereof. In some embodiments, the delayed release buffering component comprises a second buffering ingredient, an enteric agent, and a sustained-release ingredient. In some embodiments, the delayed release buffering component comprises a core, a shell surrounding the core, and a subcoat between the core and the shell, wherein the core comprises the second buffering ingredient, the shell comprises the enteric agent, and the subcoat comprises the sustained-release ingredient. In some embodiments, the delayed release buffering component comprises a second buffering ingredient, an enteric agent, and a second acid-soluble ingredient. In some embodiments, the delayed release buffering component comprises a core, a shell surrounding the core, and a subcoat between the core and the shell, wherein the core comprises the second buffering ingredient, the shell comprises the enteric agent, and the subcoat comprises the second acid-soluble ingredient. In some embodiments, the second acid soluble ingredient comprises calcium carbonate, a cationic copolymer, or combinations thereof. In some embodiments, the cationic copolymer comprises one or more of dimethylaminoethyl methacrylate, butyl methacrylate, and methyl methacrylate. In some embodiments, the second acid soluble ingredient is the same as the first acid soluble ingredient. In some embodiments, the second buffering ingredient comprises calcium carbonate, sodium bicarbonate, magnesium oxide, tribasic sodium phosphate, or combinations thereof. In some embodiments, the second buffering ingredient is the same as the first buffering ingredient. In some embodiments, the enteric ingredient comprises one or more of shellac, methyl acrylate-methacrylic acid copolymers, cellulose acetate phthalate, cellulose acetate succinate, hydroxypropyl methyl cellulose phthalate, hypromellose acetate succinate, polyvinyl acetate phthalate, sodium alginate, and zein.

In some embodiments, the invention relates to a dosage form including an abuse deterrent pharmaceutical composition including a drug susceptible to abuse; a first acid soluble ingredient; a first buffering ingredient; and a delayed release buffering component. In some embodiments, the composition further includes an ingredient for decreasing gastric acid production. In some embodiments, the ingredient for decreasing gastric acid production comprises an H2-antagonist. In some embodiments, the H2-antagonist is present in an amount that is 10-50% of the lowest therapeutic dose of the H2 antagonist for reducing stomach acid secretion. In some embodiments, the composition further includes an ingredient for increasing gastric emptying time. In some embodiments, the ingredient for increasing gastric emptying time is selected from the group consisting of a monosaccharide, a disaccharide, an oligosaccharide, a polysaccharide, an amino acid, a peptide, a protein, a fatty acid, a monoglyceride, a diglyceride, and a triglyceride. In some embodiments, the ingredient for increasing gastric emptying time is selected from the group consisting of loperamide, diphenoxylate, atropine, difenoxin, an anticholinergic, an antidepressant, an opioid, an antidiarrheal drug, and a gastroparesis inducing drug. In some embodiments, upon ingestion by a subject, the ingredient for increasing gastric emptying time increases the gastric emptying time of the subject. In some embodiments, the first acid soluble ingredient includes calcium carbonate, a cationic copolymer, or a combination thereof. In some embodiments, the cationic copolymer includes one or more of dimethylaminoethyl methacrylate, butyl methacrylate, and methyl methacrylate. In some embodiments, the first buffering ingredient includes calcium carbonate, sodium bicarbonate, magnesium oxide, tribasic sodium phosphate, or combinations thereof. In some embodiments, the delayed release buffering component comprises a second buffering ingredient, an enteric agent, and a sustained-release ingredient. In some embodiments, the delayed release buffering component comprises a core, a shell surrounding the core, and a subcoat between the core and the shell, wherein the core comprises the second buffering ingredient, the shell comprises the enteric agent, and the subcoat comprises the sustained-release ingredient. In some embodiments, the delayed release buffering component comprises a second buffering ingredient, an enteric agent, and a second acid-soluble ingredient. In some embodiments, the delayed release buffering component comprises a core, a shell surrounding the core, and a subcoat between the core and the shell, wherein the core comprises the second buffering ingredient, the shell comprises the enteric agent, and the subcoat comprises the second acid-soluble ingredient. In some embodiments, the second acid soluble ingredient comprises calcium carbonate, a cationic copolymer, or combinations thereof. In some embodiments, the cationic copolymer comprises one or more of dimethylaminoethyl methacrylate, butyl methacrylate, and methyl methacrylate. In some embodiments, the second acid soluble ingredient is the same as the first acid soluble ingredient. In some embodiments, the second buffering ingredient comprises calcium carbonate, sodium bicarbonate, magnesium oxide, tribasic sodium phosphate, or combinations thereof. In some embodiments, the second buffering ingredient is the same as the first buffering ingredient. In some embodiments, the enteric ingredient comprises one or more of shellac, methyl acrylate-methacrylic acid copolymers, cellulose acetate phthalate, cellulose acetate succinate, hydroxypropyl methyl cellulose phthalate, hypromellose acetate succinate, polyvinyl acetate phthalate, sodium alginate, and zein. In some embodiments, the dosage form is a food bar or a beverage.

In some embodiments, the invention relates to a method of treating a disease alleviated by a drug susceptible to abuse, including: administering to a subject in need thereof an abuse deterrent pharmaceutical composition including a drug susceptible to abuse; a first acid soluble ingredient; a first buffering ingredient; and a delayed release buffering component. In some embodiments, the composition further includes an ingredient for decreasing gastric acid production. In some embodiments, the ingredient for decreasing gastric acid production comprises an H2-antagonist. In some embodiments, the H2-antagonist is present in an amount that is 10-50% of the lowest therapeutic dose of the H2 antagonist for reducing stomach acid secretion. In some embodiments, the ingredient for decreasing gastric acid production comprises an H2-antagonist. In some embodiments, the H2-antagonist is present in an amount that is 10-50% of the lowest therapeutic dose of the H2 antagonist for reducing stomach acid secretion. In some embodiments, the composition further includes an ingredient for increasing gastric emptying time. In some embodiments, the ingredient for increasing gastric emptying time is selected from the group consisting of a monosaccharide, a disaccharide, an oligosaccharide, a polysaccharide, an amino acid, a peptide, a protein, a fatty acid, a monoglyceride, a diglyceride, and a triglyceride. In some embodiments, the ingredient for increasing gastric emptying time is selected from the group consisting of loperamide, diphenoxylate, atropine, difenoxin, an anticholinergic, an antidepressant, an opioid, an antidiarrheal drug, and a gastroparesis inducing drug. In some embodiments, upon ingestion by a subject, the ingredient for increasing gastric emptying time increases the gastric emptying time of the subject. In some embodiments, the first acid soluble ingredient includes calcium carbonate, a cationic copolymer, or a combination thereof. In some embodiments, the cationic copolymer includes one or more of dimethylaminoethyl methacrylate, butyl methacrylate, and methyl methacrylate. In some embodiments, the first buffering ingredient includes calcium carbonate, sodium bicarbonate, magnesium oxide, tribasic sodium phosphate, or combinations thereof. In some embodiments, the delayed release buffering component comprises a second buffering ingredient, an enteric agent, and a sustained-release ingredient. In some embodiments, the delayed release buffering component comprises a core, a shell surrounding the core, and a subcoat between the core and the shell, wherein the core comprises the second buffering ingredient, the shell comprises the enteric agent, and the subcoat comprises the sustained-release ingredient. In some embodiments, the delayed release buffering component comprises a second buffering ingredient, an enteric agent, and a second acid-soluble ingredient. In some embodiments, the delayed release buffering component comprises a core, a shell surrounding the core, and a subcoat between the core and the shell, wherein the core comprises the second buffering ingredient, the shell comprises the enteric agent, and the subcoat comprises the second acid-soluble ingredient. In some embodiments, the second acid soluble ingredient comprises calcium carbonate, a cationic copolymer, or combinations thereof. In some embodiments, the cationic copolymer comprises one or more of dimethylaminoethyl methacrylate, butyl methacrylate, and methyl methacrylate. In some embodiments, the second acid soluble ingredient is the same as the first acid soluble ingredient. In some embodiments, the second buffering ingredient comprises calcium carbonate, sodium bicarbonate, magnesium oxide, tribasic sodium phosphate, or combinations thereof. In some embodiments, the second buffering ingredient is the same as the first buffering ingredient. In some embodiments, the enteric ingredient comprises one or more of shellac, methyl acrylate-methacrylic acid copolymers, cellulose acetate phthalate, cellulose acetate succinate, hydroxypropyl methyl cellulose phthalate, hypromellose acetate succinate, polyvinyl acetate phthalate, sodium alginate, and zein. In some embodiments, the method further includes administering a composition for increasing gastric emptying time, wherein the abuse deterrent pharmaceutical composition is administered before the composition for increasing gastric emptying time, after the composition for increasing gastric emptying time, or simultaneously with the composition for increasing gastric emptying time. In some embodiments, the ingredient for increasing gastric emptying time is selected from the group consisting of a monosaccharide, a disaccharide, an oligosaccharide, a polysaccharide, an amino acid, a peptide, a protein, a fatty acid, a monoglyceride, a diglyceride, and a triglyceride. In some embodiments, the ingredient for increasing gastric emptying time is selected from the group consisting of loperamide, diphenoxylate, atropine, difenoxin, an anticholinergic, an antidepressant, an opioid, an antidiarrheal drug, and a gastroparesis inducing drug. In some embodiments, the composition for increasing gastric emptying time is included in a dosage form, wherein the dosage form is a food bar or a beverage.

In one embodiment, the invention relates to an abuse deterrent pharmaceutical composition including a drug susceptible to abuse, an acid soluble ingredient, a buffering ingredient, and an ingredient for increasing gastric emptying time.

In some embodiments, the acid soluble ingredient forms a matrix, and a substantial portion of the drug susceptible to abuse is contained within the matrix. In some embodiments, the acid soluble ingredient comprises calcium carbonate, a cationic copolymer, or combinations thereof. In some embodiments, the cationic copolymer comprises one or more of dimethylaminoethyl methacrylate, butyl methacrylate, and methyl methacrylate. In some embodiments, the acid soluble ingredient is present in an amount of about 1 wt % to about 40 wt % of the pharmaceutical composition. In some embodiments, the buffering ingredient comprises calcium carbonate, sodium bicarbonate, magnesium oxide, tribasic sodium phosphate, or combinations thereof. In some embodiments, the buffering ingredient is present in an amount of about 45 wt % to about 95 wt %.

In one embodiment, the invention relates to an abuse deterrent pharmaceutical composition including a drug susceptible to abuse, an acid soluble ingredient, a buffering ingredient, and an ingredient for increasing gastric emptying time which can be a monosaccharide, a disaccharide, an oligosaccharide, a polysaccharide, an amino acid, a peptide, a protein, a fatty acid, a monoglyceride, a diglyceride, or a triglyceride. In one embodiment, the invention relates to an abuse deterrent pharmaceutical composition including a drug susceptible to abuse, an acid soluble ingredient, a buffering ingredient, and an ingredient for increasing gastric emptying time which can be loperamide, diphenoxylate, atropine, difenoxin, an anticholinergic, an antidepressant, an opioid, an antidiarrheal drug, and a gastroparesis inducing drug.

In one embodiment, the invention relates to an abuse deterrent pharmaceutical composition including a drug susceptible to abuse, an acid soluble ingredient, a buffering ingredient, and an ingredient for increasing gastric emptying time, wherein upon ingestion by a subject, the ingredient for increasing gastric emptying time increases the gastric emptying time of the subject. In one embodiment, the invention relates to an abuse deterrent pharmaceutical composition including a drug susceptible to abuse, an acid soluble ingredient, a buffering ingredient, and an ingredient for increasing gastric emptying time, wherein upon ingestion by a subject, the ingredient for increasing gastric emptying time increases the gastric emptying time of the composition.

In one embodiment, the invention relates to an abuse deterrent pharmaceutical composition including a drug susceptible to abuse, an acid soluble ingredient, a buffering ingredient, and an ingredient for increasing gastric emptying time, wherein the acid soluble ingredient and the buffering ingredient retard release of the drug when the composition is ingested in excess of an intended dosage.

In one embodiment, the invention relates to a dosage form including an abuse deterrent pharmaceutical composition including a drug susceptible to abuse, an acid soluble ingredient, a buffering ingredient, and an ingredient for increasing gastric emptying time. In some embodiments, the dosage form is a food bar or a beverage.

In one embodiment, the invention relates to a method of treating a disease alleviated by a drug susceptible to abuse, including administering to a subject in need thereof an abuse deterrent pharmaceutical composition including a drug susceptible to abuse, an acid soluble ingredient, a buffering ingredient, and an ingredient for increasing gastric emptying time.

In one embodiment, the invention relates to a method of treating a disease alleviated by a drug susceptible to abuse, including administering to a subject in need thereof a dosage form comprising an abuse deterrent pharmaceutical composition including a drug susceptible to abuse, an acid soluble ingredient, a buffering ingredient, and an ingredient for increasing gastric emptying time. In some embodiments, the dosage form is a food bar or a beverage.

In one embodiment, the invention relates to a method of treating a disease alleviated by a drug susceptible to abuse, including administering to a subject in need thereof an abuse deterrent pharmaceutical composition comprising a drug susceptible to abuse, an acid soluble ingredient, and a buffering ingredient, and a composition for increasing gastric emptying time including an ingredient for increasing gastric emptying time. In some embodiments, the abuse deterrent pharmaceutical composition is administered before the composition for increasing gastric emptying time. In some embodiments, the abuse deterrent pharmaceutical composition is administered after the composition for increasing gastric emptying time. In some embodiments, the abuse deterrent pharmaceutical composition is administered simultaneously with the composition for increasing gastric emptying time. In some embodiments, the ingredient for increasing gastric emptying time is a monosaccharide, a disaccharide, an oligosaccharide, a polysaccharide, an amino acid, a peptide, a protein, a fatty acid, a monoglyceride, a diglyceride, or a triglyceride. In some embodiments, the ingredient for increasing gastric emptying time is loperamide, diphenoxylate, atropine, difenoxin, an anticholinergic, an antidepressant, an opioid, an antidiarrheal drug, or a gastroparesis inducing drug.

In one embodiment, the invention relates to a method of treating a disease alleviated by a drug susceptible to abuse, including administering to a subject in need thereof an abuse deterrent pharmaceutical composition comprising a drug susceptible to abuse, an acid soluble ingredient, and a buffering ingredient, and a dosage form including a composition for increasing gastric emptying time including an ingredient for increasing gastric emptying time, wherein the dosage form is a food bar or a beverage.

BRIEF DESCRIPTION OF THE DRAWINGS

The present invention will be better understood by examining the following figures which illustrate certain properties of the present invention.

DETAILED DESCRIPTION OF THE INVENTION

The compositions and methods of the invention relate to self-regulated dosages, in particular self-regulated dosages of drugs susceptible to abuse. The self-regulated dosages of the invention rely on a multiple technological approach. The dosages self-regulate first by modulating, for example increasing or decreasing, the pH of a surrounding medium, typically the gastric content of a subject. The change in pH in turn controls the release of the active ingredient from the composition included in the dosage. Thus, if the total amount of the dosage exceeds a certain limit, typically the limit at which the drug or active ingredient is prescribed for its normal therapeutic use, the change in pH relative to the normal pH range slows down the release of the active ingredient, typically by delaying or stopping the disintegration of a matrix element which is included with the active ingredient, for example by enveloping or sequestering the active ingredient. In some embodiments the dosages further include a delayed release buffering component that prolongs the effect of delaying or stopping the release of the active ingredient from the matrix when an excess dose is ingested. In some embodiments the dosages further self-regulate by increasing the gastric emptying time, thus increasing the time available for the pH modulation self-regulation mechanism to act and enhancing its overall effects.

A self-regulated dosage is designed to limit, and prolong, the absorption of drugs when inappropriate doses are ingested, or the medication is abused. Ingredients in self-regulated tablets include antacids/buffering agents to change, for example increase, the stomach pH upon oral administration. In some embodiments, the drug susceptible to abuse is included in dosage forms that are intended to dissolve in an acidic gastric medium having a pH of 5 or less, and deliver an immediate-release, or extended-release profile of the active ingredient drug when an intended, or typically prescribed dose, for example one or two unit doses, is ingested. Conversely, the self-regulated dosage forms are intended to neutralize gastric pH as more tablets are ingested retarding the release of active ingredient at pH above 5.

In some embodiments, formulations of the present invention are designed to block or thwart the effects caused by intentional or unintentional over-ingestion of drug products. Under normal dosing conditions the inventive formulations may allow for the complete oral delivery of the desired drug dose. However when excess doses are ingested, for example doses exceeding the doses typically prescribed for normal therapeutic use, either intentionally or unintentionally, the inventive formulations can work to either slow or block the release and subsequent absorption of the excessive doses. Thus, in the case of intentional excess oral consumption where a drug abuser would consume excess doses of an abused drug to experience a "high", the "high" would be significantly reduced for the inventive formulations compared to doses which freely release the excess drug of abuse. In this way, the inventive formulation may work as a deterrent from abusing the inventive formulations for the purpose of getting high. Yet the patient who uses the invention as directed or prescribed will receive the desired therapeutic effect or treatment.

In general, and as described in more detail herein, pharmaceutical formulations of the present invention may be designed with one or more components to control release and/or absorption of an active pharmaceutical ingredient. In some embodiments, a pharmaceutical formulation may be designed with a pH modifying feature and/or a pH dependent solubility feature. A pH modifying feature may impact release and/or absorption of an active ingredient by modifying the pH of the gastric environment based on whether the pharmaceutical composition is taken at an appropriate dosage amount or in excess. A pH modifying feature may be provided by inclusion of one or more buffering and/or antacid ingredients in the pharmaceutical composition. A pH modifying feature may be provided by inclusion of a buffering ingredient (e.g., an immediate release buffering ingredient and a delayed release buffering ingredient). A pH dependent solubility feature may impact release and/or absorption of an active ingredient by containing or releasing the active pharmaceutical ingredient, depending on the pH of the gastric environment. A pH dependent solubility feature may be provided by inclusion in the pharmaceutical composition of one or more acid soluble ingredients. Pharmaceutical compositions including acid soluble ingredients are described in U.S. Pat. Nos. 9,662,393, 9,320,796, and 9,101,636, and U.S. Patent Application Publication No. 20170056501, all of which are incorporated by reference herein in their entireties.

In some embodiments, the compositions and methods of the invention synergistically incorporate an additional mechanism of self-regulation, which include increasing the gastric emptying time in a subject which ingested a composition disclosed herein.

Without wishing to be bound by any particular theory, certain embodiments of the invention rely in part on the observation that in-vivo administration of one or more dosages of a self-regulated composition lacking a gastric emptying time increasing mechanism results in a non-linear response in terms of the observed $C_{max}$ of the corresponding active ingredient. For example, as described in Example 1, the in-vivo reduction in $C_{max}$ resulting from eight tablets was approximately the same as with 3 tablets, despite the fact that the 8 tablets corresponded to 2.7 times more buffering capacity of the gastric environment compared to the 3 tablets. Thus, although a sufficient level of buffer can be provided in a certain number of tablets, the effect and duration of the in-vivo self-regulating buffer level can be synergistically affected by additional mechanisms, such as the gastric emptying time. If the buffer on which the first self-regulation mechanism relies has a relatively short duration, e.g., approximately 25 minutes, in the stomach, then in some cases the buffer can be emptied out of the stomach before it can further neutralize newly produced gastric acid. Thus, the full buffer effect of multiple tablets is not realized in some cases, and the gastric fluid returns to acidic pH in the same time as with a smaller number of tablets. In some embodiments, an acid neutralization model has been employed, showing that an extended high gastric pH (>5) can be achieved if gastric emptying time is increased. In some embodiments a delayed release buffering composition model is employed, prolonging the high gastric pH (>5). This invention describes methods and compositions for increasing gastric emptying to facilitate better performance for reduction in peak plasma drug levels ($C_{max}$) for multiple tablet administrations of self-regulated dosages.

Definitions

As used herein, the term "$C_{max}$" refers to the maximum (or peak) serum concentration that a drug achieves in a specified compartment or test area of the body after the drug has been administered and before the administration of a second dose. As used herein, the term "$T_{max}$" refers to the time at which the $C_{max}$ is observed.

As used herein, the term "bioequivalence" is understood to mean one or more of 90% confidence intervals (log transformed) for $C_{max}$, or area under the concentration curve "AUC" of a drug is within 80% to 125% of the same marker for a referenced drug.

As used herein, a compound or drug having a "narrow therapeutic index" (NTI) means a compound or drug falling within any definition of narrow therapeutic index as promulgated by the U.S. Food and Drug Administration, or any successor agency thereof, for example, a substance having a less than 2-fold difference in median toxic dose (TD50) and median effective dose (ED50) values, or having a less than 2-fold difference in the minimum toxic concentration and minimum effective concentration in the blood.

When ranges are used herein to describe, for example, concentrations or amounts, all combinations and subcombinations of ranges and specific embodiments therein are intended to be included. Use of the term "about" when referring to a number or a numerical range means that the number or numerical range referred to is an approximation within experimental variability, or within statistical experimental error, and thus the number or numerical range may vary. The variation is typically from 0% to 5%, from 0% to 10%, from 0% to 15%, or the like, of the stated number or numerical range. For example, "about 45%" is understood to include 40.5% to 49.5%.

The term "comprising," and related terms such as "comprise," "comprises," "having," or "including," includes those embodiments such as, for example, an embodiment of any composition of matter, method or process that "consist of" or "consist essentially of" the described features.

The term "gastric emptying time" means the time required to empty or move ingested material out of the stomach. The time is measured from when the material is swallowed until the material moves into small intestine. Similarly, the term "gastric residence time" means the time material remains in the stomach from when it is ingested until it moves into the small intestine.

Abuse Deterrent Pharmaceutical Compositions

In one embodiment, the invention relates to an abuse deterrent pharmaceutical composition including a drug susceptible to abuse, a first acid soluble ingredient, a first buffering ingredient, and a delayed release buffering component.

In one embodiment, the invention relates to an abuse deterrent pharmaceutical composition including a drug susceptible to abuse, an acid soluble ingredient, a buffering ingredient, and an ingredient for increasing gastric emptying time.

In one embodiment, the invention relates to an abuse deterrent pharmaceutical composition including a drug susceptible to abuse, an acid soluble ingredient, a buffering ingredient, and an ingredient for decreasing the production of gastric acid.

In one embodiment, the invention relates to an abuse deterrent pharmaceutical composition including a drug susceptible to abuse, a first acid soluble ingredient, a first buffering ingredient, an ingredient for decreasing the production of gastric acid, and a delayed release buffering component.

In one embodiment, the invention relates to an abuse deterrent pharmaceutical composition including a drug susceptible to abuse, a first acid soluble ingredient, a first buffering ingredient, an ingredient for increasing gastric emptying time, and a delayed release buffering component.

In one embodiment, the invention relates to an abuse deterrent pharmaceutical composition including a drug susceptible to abuse, a first acid soluble ingredient, a first buffering ingredient, an ingredient for decreasing the production of gastric acid, and an ingredient for increasing gastric emptying time.

In one embodiment, the invention relates to a pharmaceutical composition including a drug (e.g., a drug susceptible to abuse), and one or more of a) a first acid soluble ingredient, b) a first buffering ingredient, c) an ingredient for increasing gastric emptying time, d) an ingredient for decreasing production of gastric acid, and e) a delayed release buffering component.

Active Pharmaceutical Ingredients

Any drug, therapeutically acceptable drug salt, drug derivative, drug analog, drug homologue, prodrug, or polymorph can be used in the present invention. Suitable drugs for use with the present invention can be found in the Physician's Desk Reference, 59th Edition, the content of which is hereby incorporated by reference. In one embodiment, the drug is an orally administered drug. In some embodiments a pharmaceutical composition in accordance with the present invention can include a mixture, coated particle, or granule of one or more drugs, therapeutically acceptable drug salts, drug derivatives, drug analogs, drug homologues, or polymorphs.

In certain embodiments, drugs susceptible to abuse are used. Drugs commonly susceptible to abuse include psychoactive drugs and analgesics, including but not limited to opioids, opiates, stimulants, tranquilizers, sedatives, anxiolytics, narcotics and drugs that can cause psychological and/or physical dependence. In one embodiment, the drug for use in the present invention can include amphetamines, amphetamine-like compounds, benzodiazepines, and methylphenidate or combinations thereof. In another embodiment, the present invention can include any of the resolved isomers of the drugs described herein, and/or salts thereof.

A drug for use in the present invention can be a drug with narrow therapeutic index. Upon administration, too little of the narrow therapeutic index drug in the blood stream can lead to insufficient therapeutic activity, while a too large dose of the narrow therapeutic index drug can lead to excessive therapeutic activity or toxicity, both of which can be detrimental. As a result, the use of narrow therapeutic index drugs must be carefully monitored, and their potential abuse deterred.

A drug for use in the present invention can be a drug susceptible to abuse. A drug for use in the present invention which can be susceptible to abuse can be one or more of the following: alfentanil, amphetamines, buprenorphine, butorphanol, carfentanil, codeine, dezocine, diacetylmorphine, dihydrocodeine, dihydromorphine, diphenoxylate, diprenorphine, etorphine, fentanyl, hydrocodone, hydromorphone, β-hydroxy-3-methylfentanyl, levo-α-acetylmethadol, levorphanol, lofentanil, meperidine, methadone, methylphenidate, morphine, nalbuphine, nalmefene, oxycodone, oxymorphone, pentazocine, pethidine, propoxyphene, remifentanil, sufentanil, tilidine, and tramadol, salts, derivatives, analogs, homologues, polymorphs thereof, and mixtures of any of the foregoing.

In another embodiment a drug for use with the present invention which can be susceptible to abuse includes one or more of the following: dextromethorphan (3-Methoxy-17-methy-9a, 13a, 14a-morphinan hydrobromide monohydrate), N-{1-[2-(4-ethyl-5-oxo-2-tetrazolin-1-yl)-ethyl]-4-methoxymethyl-4-piperidyl} propionanilide (alfentanil), 5,5-diallyl barbituric acid (allobarbital), allylprodine, alphaprodine, 8-chloro-1-methyl-6-phenyl-4H-[1,2,4]triazolo[4,3-a][1,4]-benzodiazepine (alprazolam), 2-diethylaminopropiophenone (amfepramone), (±)-α-methyl phenethylamine (amphetamine), 2-(α-methylphenethyl-amino)-2-phenyl acetonitrile (amphetaminil), 5-ethyl-5-isopentyl barbituric acid (amobarbital), anileridine, apocodeine, 5,5-diethyl barbituric acid (barbital), benzylmorphine, bezitramide, 7-bromo-5-(2-pyridyl)-1H-1,4-benzodiazepin-2(3H)-one (bromazepam), 2-bromo-4-(2-chlorophenyl)-9-methyl-6H-thieno[3,2-f][1,2,4]-triazolo[4,3-a][1,4]diazepine (brotizolam), 17-cyclopropylmethyl-4,5α-epoxy-7α[(S)-1-hydroxy-1,2,2-trimethylpropyl]-6-methoxy-6,14-endo-ethanomorphinan-3-ol (buprenorphine), 5-butyl-5-ethyl barbituric acid (butobarbital), butorphanol, (7-chloro-1,3-dihydro-1-methyl-2-oxo-5-phenyl-2H-1,4-benzodiazepin-3-yl)-dimethyl carbamate (camazepam), (1S,2S)-2-amino-1-phenyl-1-propanol (cathine/D-norpseudoephedrine), 7-chloro-N-methyl-5-phenyl-3H-1,4-benzodiazepin-2-ylamine-4 oxide (chlordiazepoxide), 7-chloro-1-methyl-5-phenyl-1H-1,5-benzodiazepine-2,4(3H,5H)-dione (clobazam), 5-(2-chlorophenyl)-7-nitro-1H-1,4-benzodiazepin-2(3H)-one (clonazepam), clonitazene, 7-chloro-2,3-dihydro-2-oxo-5-phenyl-1H-1,4-benzodiazepine-3-carboxylic acid (clorazepate), 5-(2-chlorophenyl)-7-ethyl-1-methyl-1H-thieno[2,3-e][1,4]-diazepin-2(3H)-one (clotiazepam), 10-chloro-11b-(2-chlorophenyl)-2,3,7,11b-tetrahydrooxazolo[3,2-d][1,4]benzodiazepin-6(5H)-one (cloxazolam), (−)-methyl-[3β-benzoyloxy-2β(1αH,5αH)-tropane carboxylate (cocaine), 4,5α-epoxy-3-methoxy-17-methyl-7-morphinen-6α-ol (codeine), 5-(1-cyclohexenyl)-5-ethyl barbituric acid (cyclobarbital), cyclorphan, cyprenorphine, 7-chloro-5-(2-chlorophenyl)-1H-1,4-benzodiazepin-2(3H)-one (delorazepam), desomorphine, dextromoramide, (+)-(1-benzyl-3-dimethylamino-2-methyl-1-phenylpropyl) propionate (dextropropoxyphene), dezocine, diampromide, diamorphone, 7-chloro-1-methyl-5-phenyl-1H-1,4-benzodiazepin-2(3H)-one (diazepam), 4,5α-epoxy-3-methoxy-17-methyl-6α-morphinanol (dihydrocodeine), 4,5α-epoxy-17-methyl-3,6a-morphinandiol (dihydromorphine), dimenoxadol, dimephetamol [sic—Tr.Ed.], dimethyl thiambutene, dioxaphetyl butyrate, dipipanone, (6aR,10aR)-6,6, 9-trimethyl-3-pentyl-6a,7,8,10a-tetrahydro-6H-benzo[c]chromen-1-ol (dronabinol), eptazocine, 8-chloro-6-phenyl-4H-[1,2,4]triazolo[4,3-a][1,4]benzodiazepine (estazolam), ethoheptazine, ethyl methyl thiambutene, ethyl-[7-chloro-5-(2-fluorophenyl)-2,3-dihydro-2-oxo-1H-1,4-benzodiazepin-3-carboxylate] (ethyl loflazepate), 4,5α-epoxy-3-ethoxy-17-methyl-7-morphinen-6α-ol (ethylmorphine), etonitrazene, 4,5α-epoxy-7α-(1-hydroxy-1-methylbutyl)-6-methoxy-17-methyl-6,14-endo-etheno-morphinan-3-ol (etorphine), N-ethyl-3-phenyl-8,9,10-trinorbornan-2-ylamine (fencamfamine), 7-[2-(α-methylphenethylamino)-ethyl]theophylline (fenethylline), 3-(α-methylphenethylamino) propionitrile (fenproporex), N-(1-phenethyl-4-piperidyl) propionanilide (fentanyl), 7-chloro-5-(2-fluorophenyl)-1-methyl-1H-1,4-benzodiazepin-2(3H)-one (fludiazepam), 5-(2-fluorophenyl)-1-methyl-7-nitro-1H-1,4-benzodiazepin-2-(3H)-one (flunitrazepam), 7-chloro-1-(2-diethylaminoethyl)-5-(2-fluorophenyl)-1H-1,4-benzodiazepin-2(3H)-one (flurazepam), 7-chloro-5-phenyl-1-(2,2,2-trifluoroethyl)-1H-1,4-benzodiazepin-2(3H)-one (halazepam), 10-bromo-11b-(2-fluorophenyl)-2,3,7,11b-tetrahydro[1,3]oxazolo[3,2-d][1,4]benzodiazepin-6(5H)-one (haloxazolam), heroin, 4,5α-epoxy-3-methoxy-17-methyl-6-morphinanone (hydrocodone), 4,5α-epoxy-3-hydroxy-17-methyl-6-morphinanone (hydromorphone), hydroxypethidine, isomethadone, hydroxymethyl morphinan, 11-chloro-8,12b-dihydro-2,8-dimethyl-12b-phenyl-4H-[1,3]oxazino[3,2-d][1,4]benzodiazepin-4,7(6H)-dione (ketazolam), 1-[4-(3-hydroxyphenyl)-1-methyl-4-piperidyl]-1-propanone (ketobemidone), (3S,6S)-6-dimethylamino-4,4-diphenyl-heptan-3-yl acetate (levacetylmethadol (LAAM)), (−)-6-dimethylamino-4,4-diphenyl-3-heptanone (levomethadone), (−)-17-methyl-3-morphinanol (levorphanol), levophenacyl morphan, lofentanil, 6-(2-chlorophenyl)-2-(4-methyl-1-piperazinylmethylene)-8-nitro-2H-imidazo[1,2a][1,4]benzodiazepin-1(4H)-one (loprazolam), 7-chloro-5-(2-chlorophenyl)-3-hydroxy-1H-1,4-benzodiazepin-2(3H)-one (lorazepam), 7-chloro-5-(2-chlorophenyl)-3-hydroxy-1-methyl-1H-1,4-benzodiazepin-2(3H)-one (lormetazepam), 5-(4-chlorophenyl)-2,5-dihydro-3H-imidazo[2,1-a]isoindol-5-ol (mazindol), 7-chloro-2,3-dihydro-1-methyl-5-phenyl-1H-1,4-benzodiazepine (medazepam), N-(3-chloropropyl)-α-methylphenetylamine (mefenorex), meperidine, 2-methyl-2-propyl trimethylene dicarbamate (meprobamate), meptazinol, metazocine, methylmorphine, N,α-dimethylphenethylamine (methamphetamine), (±)-6-dimethylamino-4,4-diphenyl-3-heptanone (methadone), 2-methyl-3-o-tolyl-4(3H)-quinazolinone (methaqualone), methyl-[2-phenyl-2-(2-piperidyl)acetate] (methyl phenidate), 5-ethyl-1-methyl-5-phenyl barbituric acid (methyl phenobarbital), 3,3-diethyl-5-methyl-2,4-piperidinedione (methyprylon), metopon, 8-chloro-6-(2-fluorophenyl)-1-methyl-4H-imidazo[1,5-a][1,4]benzodiazepine (midazolam), 2-(benzhydrylsulfinyl) acetamide (modafinil), 4,5α-epoxy-17-methyl-7-morphinene-3,6α-diol (morphine), myrophine, (±)-trans-3-(1,1-dimethylheptyl)-7,8,10,10α-tetrahydro-1-hydroxy-6,6-dimethyl-6H-dibenzo[b,d]pyran-9(6αH)-one (nabilone), nalbuphen, nalorphine, narceine, nicomorphine, 1-methyl-7-nitro-5-phenyl-1H-1,4-benzodiazepin-2(3H)-one (nimetazepam), 7-nitro-5-phenyl-1H-1,4-benzodiazepin-2(3H)-one (nitrazepam), 7-chloro-5-phenyl-1H-1,4-benzodiazepin-2-(3H)-one (nordazepam), norlevorphanol, 6-dimethylamino-4,4-diphenyl-3-hexanone (normethadone), normorphine, norpipanone, the coagulated juice of the plants belonging to the species *Papaver somniferum* (opium), 7-chloro-3-hydroxy-5-phenyl-1H-1,4-benzodiazepin-2-(3H)-one (oxazepam), (cis-trans)-10-chloro-2,3,7, 11b-tetrahydro-2-methyl-11b-phenyloxazolo[3,2-d][1,4] benzodiazepin-6-(5H)-one (oxazolam), 4,5α-epoxy-14-hydroxy-3-methoxy-17-methyl-6-morphinanone (oxycodone), oxymorphone, plants and plant parts of the plants belonging to the species *Papaver somniferum* (including the subspecies *setigerum*) (*Papaver somniferum*), papaveretum, 2-imino-5-phenyl-4-oxazolidinone (pemoline), 1,2,3,4,5,6-hexahydro-6,11-dimethyl-3-(3-methyl-2-butenyl)-2,6-methano-3-benzazocin-8-ol (pentazocine), 5-ethyl-5-(1-methylbutyl) barbituric acid (pentobarbital), ethyl-(1-methyl-4-phenyl-4-piperidine-carboxylate) (pethidine), phenadoxone, phenomorphan, phenazocine, phenoperidine, piminodine, pholcodeine, 3-methyl-2-phenyl morpholine (phenmetrazine), 5-ethyl-5-phenyl barbituric acid (phenobarbital), α,α-dimethyl phenethylamine (phentermine), 7-chloro-5-phenyl-1-(2-propinyl)-1H-1,4-benzodiazepin-2 (3H)-one (pinazepam), α-(2-piperidyl)benzhydryl alcohol (pipradol), 1'-(3-cyano-3,3-diphenylpropyl)[1,4'-bipiperidine]-4'-carboxamide (piritramide), 7-chloro-1-(cyclopropylmethyl)-5-phenyl-1H-1,4-benzodiazepin-2(3H)-one (prazepam), profadol, proheptazine, promedol, properidine, propoxyphene, N-(1-methyl-2-piperidinoethyl)-N-(2-pyridyl) propionamide, methyl-{3-[4-methoxycarbonyl-4-(N-phenylpropaneamido)piperidino]propanoate} (remifentanil), 5-sec.-butyl-5-ethyl barbituric acid (secbutabarbital), 5-allyl-5-(1-methylbutyl) barbituric acid (secobarbital), N-{4-methoxymethyl-1-[2-(2-thienyl)ethyl]-4-piperidyl} propionanilide (sufentanil), 7-chloro-2-hydroxy-methyl-5-phenyl-1H-1,4-benzodiazepin-2-(3H)-one (temazepam), 7-chloro-5-(1-cyclohexenyl)-1-methyl-1H-1,4-benzodiazepin-2(3H)-one (tetrazepam), ethyl-(2-dimethylamino-1-phenyl-3-cyclohexane-1-carboxylate) (tilidine (cis and trans)), tramadol, 8-chloro-6-(2-chlorophenyl)-1-methyl-4H-[1,2,4]triazolo[4,3-a][1,4]benzodiazepine (triazolam), 5-(1-methylbutyl)-5-vinyl barbituric acid (vinylbital), (1R*, 2R*)-3-(3-dimethylamino-1-ethyl-2-methyl-propyl) phenol, (1R,2R,4S)-2-[dimethylamino)methyl-4-(p-fluorobenzyloxy)-1-(m-methoxyphenyl) cyclohexanol, each optionally in the form of corresponding stereoisomeric compounds as well as corresponding derivatives, especially esters or ethers, and all being physiologically compatible compounds, especially salts and solvates.

In one embodiment, a pharmaceutical composition of the present invention includes one or more opioids such as hydrocodone, morphine, oxycodone, hydromorphone and/or salts thereof, as the therapeutically active ingredient.

Typically when processed into a suitable dosage form, as described in more detail below, the drug can be present in such dosage forms in an amount normally prescribed, typically about 0.5 to about 25 percent on a dry weight basis, based on the total weight of the formulation. In some embodiments, such an amount can be typically about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 1.25 mg, about 1.5 mg, about 1.75 mg, about 2 mg, about 2.25 mg, about 2.5 mg, about 2.75 mg, about 3 mg, about 3.5 mg, about 4 mg, about 5 mg, about 6 mg, about 7 mg, about 7.5, about 10 mg, about 15 mg, about 20 mg, about 25 mg, about 50 mg, about 75 mg, about 100 mg, about 125 mg, about 150 mg, about 175 mg, or about 200 mg. More typically, the drug can be present in an amount from about 1 mg to about 10 mg, from about 2 mg to about 25 mg, from about 5 mg to about 75 mg, from about 10 mg to about 200 mg, from about 125 mg to about 250 mg, or from about 250 mg to about 500 mg. In other embodiments, a dosage form contains an appropriate amount of drug to provide a therapeutic effect.

In some embodiments, a composition of the invention includes a drug or active ingredient in an amount, on a weight basis, of about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 99.9%.

Ingredients Soluble in Acidic Solutions

In some embodiments, pharmaceutical compositions of the present invention include one or more components which are soluble in acidic solutions. Acidic solutions may be considered to be those having a pH of less than 7, about 1 to about 4, about 2 to about 5, less than or equal to 5, or the like. In some embodiments, the acid soluble component is less soluble in slightly acidic, neutral, and/or basic solutions. In some embodiments, the acid soluble component is less soluble in solutions having a pH of greater than about 4 or 5.

In some embodiments, an acid soluble component is included in a pharmaceutical composition in the form of particle matrix with an active pharmaceutical ingredient. The acid soluble ingredient may be included in the pharmaceutical composition in an amount sufficient to form this matrix. In some embodiments, the active ingredient is sequestered within the acid soluble component. The acid soluble component may impact release of the active pharmaceutical ingredient depending on the pH of the environment, which is raised or maintained by the buffering and/or antacid ingredient as a function of the amount of the pharmaceutical composition ingested: when the pharmaceutical composition is ingested in an appropriate dosage amount, the pH buffering ingredient is not present in a high enough amount to affect the gastrointestinal pH, and the acid soluble component dissolves and releases the active pharmaceutical ingredient, when the pharmaceutical component is ingested in an excess amount, the pH buffering ingredient is present in an amount to raise the gastrointestinal pH, thereby preventing the acid soluble ingredient from dissolving and releasing the active pharmaceutical ingredient.

In some embodiments, the acid soluble ingredient forms a matrix, and a substantial portion of the drug susceptible to abuse is contained within the matrix. In some embodiments, the acid soluble ingredient comprises calcium carbonate, a cationic copolymer, or combinations thereof. In some embodiments, the cationic copolymer comprises one or more of dimethylaminoethyl methacrylate, butyl methacrylate, and methyl methacrylate.

In some embodiments, the acid soluble ingredient is present in an amount of about 1 wt % to about 40 wt %, about 5 wt % to about 50 wt %, about 7.5 wt % to about 65 wt %, about 10 wt % to about 75 wt %, or about 25 wt % to about 95 wt % of the pharmaceutical composition.

In some embodiments, an acid soluble component is included in the pharmaceutical composition an amount of about 1 wt % to about 50 wt %, about 1 wt % to about 48 wt %, about 1 wt % to about 46 wt %, about 1 wt % to about 44 wt %, about 1 wt % to about 42 wt %, about 1 wt % to about 40 wt %, about 2 wt % to about 38 wt %, about 4 wt % to about 36 wt %, about 6 wt % to about 34 wt %, about 8 wt % to about 32 wt %, about 10 wt % to about 30 wt %, about 12 wt % to about 28 wt %, about 14 wt % to about 26 wt %, about 16 wt % to about 24 wt %, about 18 wt % to about 22 wt %, about 1 wt %, about 2 wt %, about 4 wt %, about 6 wt %, about 8 wt %, about 10 wt %, about 12 wt %, about 14 wt %, about 16 wt %, about 18 wt %, about 20 wt %, about 22 wt %, about 24 wt %, about 26 wt %, about 28 wt %, about 30 wt %, about 32 wt %, about 34 wt %, about 36 wt %, about 38 wt %, about 40 wt %, about 42 wt %, about 44 wt %, about 46 wt %, about 48 wt %, or about 50 wt % of the pharmaceutical composition.

In some embodiments, a composition of the invention includes an acid soluble ingredient in an amount of about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 99.9%.

Examples of suitable acid soluble components include calcium carbonate, chitosan, polymers and copolymers such as polymethacrylates, e.g., Eudragit® (cationic polymer with dimethylaminoethyl methacrylate as a functional group).

Buffering and/or Antacid Ingredients

In some embodiments, pharmaceutical compositions of the present invention include one or more buffering and/or antacid ingredients. Such ingredient(s) may result in an elevation in stomach pH if the pharmaceutical composition is consumed in adequate amounts, and/or in amounts higher than those typically prescribed for normal therapeutic use. In some embodiments, such ingredient may result in rapid and sustained elevation of stomach pH to a pH of greater than about 4 when the pharmaceutical composition is consumed in adequate amounts, and/or in amounts higher than those typically prescribed for normal therapeutic use.

Examples of suitable buffering ingredients (e.g., first buffering ingredient, second buffering ingredient, or both first and second buffering ingredients) and/or antacid ingredients include but are not limited to aluminum hydroxide, bismuth aluminate, bismuth carbonate, bismuth subcarbonate, bismuth subgallate, bismuth subnitrate, calcium carbonate, calcium phosphate, dibasic calcium phosphate, dihydroxyaluminum aminoacetate, dihydroxyaluminum sodium carbonate, glycine, magnesium glycinate, magnesium hydroxide, magnesium oxide, potassium bicarbonate, sodium bicarbonate, sodium potassium tartrate, tribasic sodium phosphate, and tricalcium phosphate.

In some embodiments, a buffering ingredient (e.g., first buffering ingredient, second buffering ingredient, or both first and second buffering ingredients) comprises calcium carbonate, sodium bicarbonate, magnesium oxide, tribasic sodium phosphate, or combinations thereof. In some embodiments, the buffering ingredient is present in an amount of about 25 wt % to about 65 wt %, about 35 wt % to about 75 wt %, about 45 wt % to about 95 wt %, about 50 wt % to about 90 wt %, or about 55 wt % to about 75 wt %, of the pharmaceutical composition.

In some embodiments, a buffering ingredient (e.g., first buffering ingredient, second buffering ingredient, or both first and second buffering ingredients) and/or antacid ingredient may be included in an amount such that stomach pH is not affected when the pharmaceutical composition is taken in appropriate therapeutic amounts, but such that stomach pH may be elevated when the pharmaceutical composition is ingested in excess amounts, e.g., amounts higher than those typically prescribed for normal therapeutic use. In some embodiments appropriate therapeutic amounts refers to 1 or 2 tablets or doses, whereas excess amounts refers to 3 or more tablets or doses. In some embodiments, a buffering and/or antacid ingredient is included in the pharmaceutical composition in an amount of about 45 wt % to about 95 wt %, about 50 wt % to about 90 wt %, about 55 wt % to about 85 wt %, about 60 wt % to about 80 wt %, about 65 wt % to about 75 wt %, about 45 wt %, about 50 wt %, about 55 wt %, about 60 wt %, about 65 wt %, about 70 wt %, about 75 wt %, about 80 wt %, about 85 wt %, about 90 wt %, or about 95 wt % of the pharmaceutical composition.

In some embodiments, a composition of the invention includes a buffering ingredient (e.g., first buffering ingredient, second buffering ingredient, or each of first and second buffering ingredients) and/or antacid ingredient in an amount of about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 99.9% by weight of the pharmaceutical composition.

In some embodiments, one ingredient may act as both an acid soluble ingredient and a buffering ingredient (e.g., first buffering ingredient, second buffering ingredient, or both first and second buffering ingredient) and/or antacid ingredient. Examples of such suitable ingredients include calcium carbonate, di- and tribasic calcium phosphate, and magnesium hydroxide.

In some embodiments pharmaceutical compositions of the present invention further include a delayed release buffering component. In some embodiments the delayed release buffering component comprises the second buffering ingredient. In some embodiments the second buffering ingredient has the same chemical composition as the first buffering ingredient, whereas in other embodiments the second buffering ingredient has a different chemical composition from the first buffering ingredient. The delayed release buffering component may be designed to provide a back-up reservoir of a buffering ingredient(s) that is not readily discharged by the stomach. In some embodiments the delayed release buffering component, unlike the first buffering ingredient (immediate release buffering component), is insoluble in the gastric environment after ingestion of an intended dose (i.e., 1 or 2 tablets). For example, in some embodiments the delayed release buffering component may be designed to act in any one or more of the following: remain in solid form, shape, and/or particle size for a period of time post-administration such that it is not readily discharged by the stomach as would be a fine powdered or solubilized immediate release buffer; or remain intact in an acidic environment such as that of the stomach after ingestion of an intended dose (i.e., 1 or 2 tablets) and release in a neutral gastric environment, such as that of a stomach after ingestion of an excessive dose (i.e., 3 or more tablets).

In some embodiments delayed release buffering component is in a solid form. In some embodiments the delayed release buffering component remains in a solid form in a neutral gastric environment (e.g., less than a pH of 5) for at least 1 minute, at least 5 minutes, at least 10 minutes, at least 15 minutes, at least 30 minutes, at least 45 minutes, at least 60 minutes, at least 90 minutes, or at least 120 minutes.

In some embodiments the delayed release buffering component has an average particle size of 250 µm or greater, about 250 µm to about 1.2 mm, or about 400 µm. In some embodiments the second buffering component (e.g., delayed buffering component) maintains its average particle size of at least 250 µm, about 250 µm to about 1.2 mm, or about 400 µm in a neutral gastric environment (e.g., >pH 5).

In some embodiments the delayed release buffering component is insoluble at a pH of 5 or less, 4.5 or less, 4 or less, about 1 to about 5, about 1 to about 4.5, about 1 to about 4, about 1, about 1.5, about 2, about 2.5, about 3, about 3.5, about 4, about 4.5, or about 5. In some embodiments the delayed release buffering component is soluble at pH of 5 or more, 5.5 or more, 6 or more, about 5 to about 14, about 5 to about 12, about 6 to about 12, about 5, about 5.5, about 6, about 6.5, about 7, about 7.5, about 8, about 8.5, about 9, about 9.5, about 10, about 10.5, about 11, about 11.5, about 12, about 12.5, about 13, about 13.5, or about 14.

In some embodiments the delayed release buffering component comprises an enteric agent. The enteric agent may be a material that is soluble at a pH of 5 or more, 5.5 or more, 6 or more, about 5 to about 14, about 5 to about 12, about 6 to about 12, about 5, about 5.5, about 6, about 6.5, about 7, about 7.5, about 8, about 8.5, about 9, about 9.5, about 10, about 10.5, about 11, about 11.5, about 12, about 12.5, about 13, about 13.5, or about 14. Examples of suitable enteric agents include, but are not limited to, one or more of shellac, methyl acrylate-methacrylic acid copolymers, cellulose acetate phthalate, cellulose acetate succinate, hydroxypropyl methyl cellulose phthalate, hypromellose acetate succinate, polyvinyl acetate phthalate, sodium alginate, shellac, and zein.

In some embodiments the delayed release buffering component comprises a core and a shell that surrounds or substantially surrounds the core. In some embodiments the shell comprises the enteric agent of the delayed release buffering component. In some embodiments the core comprises the second buffering ingredient of the delayed release buffering component.

In some embodiments the delayed release buffering component further comprises a subcoating. The subcoating may provide sustained release properties to the material in the core, such as a second buffering ingredient in the core. Suitable materials for the subcoating include, but are not limited to copovidone, hydroxypropylcellulose, hydroxypropylmethyl cellulose, methylcellulose, povidone, and mixtures thereof. In some embodiments the subcoating is used to separate the enteric agent from the second buffering ingredient. In certain embodiments comprising a shell that includes the enteric agent and a core that includes the second buffering ingredient, the subcoating may separate the shell from the core.

In some embodiments the second buffering ingredient comprises a plurality of particles, In other embodiments the second buffering ingredient comprises a plurality of granules. In still other embodiments the second buffering ingredient comprises a tablet.

In some embodiments an acid soluble ingredient (e.g., a second acid soluble ingredient) is interspersed with, coats, surrounds, or substantially coats or substantially surrounds the second buffering ingredient. In some embodiments including a core comprising the second buffering ingredient, the core may further comprise an acid soluble ingredient (e.g., a second acid soluble component). Such acid soluble component (e.g., second acid soluble component) may delay complete release of the second buffering component in the same way the first acid soluble component delays release of the active pharmaceutical ingredient. For example, the acid soluble ingredient (e.g., second acid soluble ingredient) may delay release of the second buffering ingredient until passage of the first buffering ingredient from the gastric environment and/or acid secretion of the stomach lowers the pH once again to acidic conditions, e.g. below about 5, below about 4.5, below about 4, etc. In some embodiments an acid soluble ingredient (e.g., second acid soluble component) is a neutral or acid-soluble polymer. Suitable neutral or acid-soluble polymers include, but are not limited to methacrylate co-polymers, e.g., amino methacrylate copolymer (Eudragit RS and RL), butyl methacrylate, methyl methacrylate, dimethylaminoethyl methacrylate copolymer (Eudragit E), ethylcellulose, and ethyl acrylate-methyl methacrylate copolymer (Eudragit NE).

Ingredients for Increasing Gastric Emptying Time

In some embodiments, it has been found that increasing the gastric emptying time (i.e., increasing the time the components of the dosage form reside in the stomach before passing to the small intestine) associated with a self-regulating abuse deterrent dosage form synergistically improves the abuse deterrence characteristics of the dosage form.

Generally, any ingredient suitable for increasing gastric emptying time can be used in the compositions and methods of the invention. In some embodiments, the ingredient for increasing gastric emptying time can be a monosaccharide, a disaccharide, an oligosaccharide, a polysaccharide, an amino acid, a peptide, a protein, a fatty acid, a monoglyceride, a diglyceride, or a triglyceride. In general, most food stuff is suitable as ingredients for increasing gastric emptying time, including polysaccharides such as starches, fats such as vegetal or animal fats, and proteins such as vegetal or animal proteins.

Ingredient useful for increasing gastric emptying time can also be any drugs or active ingredients known to act as gastric emptying time increasing agents. In some embodiments, ingredients for increasing gastric emptying time can be loperamide, diphenoxylate, atropine, difenoxin, an anticholinergic, an antidepressant, an opioids, an antidiarrheal drug, and/or a gastroparesis inducing drug.

In some embodiments, an ingredient useful for increasing gastric emptying time can be a substance that delays onset of the housekeeping wave of the interdigestive myoelectric motor cycle (IMMC). Examples of agents for delaying onset of the housekeeping wave, preferably locally delivered by the dosage form in amounts not resulting in any substantial systemic effect to the subject, as for example, anticholinergic agents such as propantheline, and other agents including, but not limited to, methylcellulose, guar gum, fats such as triglyceride esters, e.g., triethanol myristate, fatty acids of 10-15 carbon atoms, and the like.

In some embodiments, the present invention includes an ingredient for increasing gastric emptying time in an amount sufficient to reduce $C_{max}$ and/or delay the onset of $C_{max}$ by a time period 1, 2, 5, 10, 15, 20, 25, 30, 35, 40, 45, 50, 55, or 60 minutes when the dosage form is abused. In one embodiment, this occurs when three or more dosage forms are consumed at or nearly simultaneously.

In some embodiments, a composition of the invention includes an ingredient for increasing gastric emptying time in a weight percent of the composition or finished dosage form of from about 1% to about 15%, from about 2.5% to about 25%, from about 5% to about 35%, from about 7.5% to about 45%, from about 10% to about 50%, from about 12.5% to about 60%, from about 15% to about 65%, from about 17.5% to about 70%, from about 20% to about 75%, from about 22.5% to about 80%, from about 25% to about 90%, from about 35% to about 95%, from about 50% to about 99%, or from about 75% to about 99.9%.

In some embodiments, a composition of the invention includes an ingredient for increasing gastric emptying time in a weight percent amount of the composition or finished dosage form of about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 99.9%.

Ingredients for Decreasing Production of Gastric Acid

Generally, any ingredients suitable for decreasing the production of gastric acid can be used in the compositions and methods of the invention. In some embodiments, the ingredient for decreasing the production of gastric acid can be a histamine 2 receptor (H2) antagonist. In some embodiments, an H2 antagonist is one or more of nizatidine, famotidine, ranitidine, and cimetidine. In some embodiments, the ingredient for decreasing the production of gastric acid can be a proton pump inhibitor. In some embodiments, a proton pump inhibitor is one or more of ilaprazole, rabeprazole, pantoprazole, esomeprazole, dexlansoprazole, lansoprazole, and omeprazole.

In some embodiments, pharmaceutical compositions of the present invention include one or more ingredients that decrease the production of gastric acid (i.e., a gastric acid secretion inhibitor). In some embodiments inclusion of an ingredient that decreases the production of gastric acid synergistically improves the abuse deterrence characteristics of the dosage form. In some embodiments the ingredient that decreases the production of gastric acid is present in an amount that is sub-therapeutic when an intended dose (e.g., 1 or 2 tablets) is ingested, but is present in a therapeutic amount when greater than an intended dose (e.g., 3 or more, such as 4, 5, 6, 7, or 8 tablets) are ingested. A therapeutic dose of gastric acid secretion inhibitor, such as provided when greater than an intended dose of pharmaceutical compositions of some embodiments of the present invention are ingested, may delay the time to stomach re-acidification.

In some embodiments the ingredient that decreases the production of gastric acid is in a core that is surrounded or substantially surrounded by a shell. In some embodiments the shell comprises an enteric agent. The enteric agent may be a material that is soluble at a pH of 5 or more, 5.5 or more, 6 or more, about 5 to about 14, about 5 to about 12, about 6 to about 12, about 5, about 5.5, about 6, about 6.5, about 7, about 7.5, about 8, about 8.5, about 9, about 9.5, about 10, about 10.5, about 11, about 11.5, about 12, about 12.5, about 13, about 13.5, or about 14. Examples of suitable enteric agents include, but are not limited to, one or more of shellac, methyl acrylate-methacrylic acid copolymers, cellulose acetate phthalate, cellulose acetate succinate, hydroxypropyl methyl cellulose phthalate, hypromellose acetate succinate, polyvinyl acetate phthalate, sodium alginate, shellac, and zein In some embodiments the inclusion of one or more ingredients that decrease the production of gastric acid invoke acid reduction at about 15 minutes, about 20 minutes, about 25 minutes, about 30 minutes, about 35 minutes, about 40 minutes, or about 45 minutes after administration.

In some embodiments, a composition of the invention includes an ingredient for decreasing the production of gastric acid in a weight percent of the composition or finished dosage form of from about 0.01% to about 1%, from about 0.01% to about 0.5%, from about 0.01% to about 0.1%, from about 0.01% to about 0.05%, from about 0.05% to about 1%, from about 0.05% to about 0.5%, from about 0.05% to about 0.1%, from about 1% to about 15%, from about 2.5% to about 25%, from about 5% to about 35%, from about 7.5% to about 45%, from about 10% to about 50%, from about 12.5% to about 60%, from about 15% to about 65%, from about 17.5% to about 70%, from about 20% to about 75%, from about 22.5% to about 80%, from about 25% to about 90%, from about 35% to about 95%, from about 50% to about 99%, or from about 75% to about 99.9%.

In some embodiments, a composition of the invention includes an ingredient for decreasing the production of gastric acid in a weight percent amount of the composition or finished dosage form of about 0.01%, about 0.02%, about 0.03%, about 0.04%, about 0.05%, about 0.06%, about 0.07%, about 0.08%, about 0.09%, about 0.1%, about 0.15%, about 0.2%, about 0.25%, about 0.3%, about 0.35%, about 0.4%, about 0.45%, about 0.5%, about 0.55%, about 0.6%, about 0.65%, about 0.75, about 0.75%, about 0.8%, about 0.85%, about 0.9%, about 0.95%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 99.9%.

Additional Ingredients

The present invention can also optionally include other ingredients to enhance dosage form manufacture from a pharmaceutical composition of the present invention and/or alter the release profile of a dosage forming including a pharmaceutical composition of the present invention.

Some embodiments of the present invention include one or more pharmaceutically acceptable fillers/diluents. In one embodiment, Avicel PH (Microcrystalline cellulose) is a filler used in the formulation. The Avicel PH can have an average particle size ranging from 20 to about 200 µm, preferably about 100 µm. The density ranges from 1.512-1.668 g/cm$^3$. The Avicel PH should have molecular weight of about 36,000. Avicel PH effectiveness is optimal when it is present in an amount of from about 10 to 65 percent, by weight on a solid basis, of the formulation. Typical fillers can be present in amounts from 10 to 65 percent by weight on a dry weight basis of the total composition. Other ingredients can include sugars and/or polyols. Lactose having a particle size of about 20 to about 400 microns and a density of about 0.3 to about 0.9 g/ml can also be included.

In some embodiments of the invention, a filler also functions as a binder in that it not only imparts cohesive properties to the material within the formulation, but can also increase the bulk weight of a directly compressible formulation (as described below) to achieve an acceptable formulation weight for direct compression. In some embodiments, additional fillers need not provide the same level of cohesive properties as the binders selected, but can be capable of contributing to formulation homogeneity and resist segregation from the formulation once blended. Further, preferred fillers do not have a detrimental effect on the flowability of the composition or dissolution profile of the formed tablets.

In one embodiment, the present invention can include one or more pharmaceutically acceptable disintegrants. Such disintegrants are known to a skilled artisan. In the present invention, disintegrants can include, but are not limited to, sodium starch glycolate (Explotab®) having a particle size of about 104 microns and a density of about 0.756 g/ml, starch (e.g., Starch 21) having a particle size of about 2 to about 32 microns and a density of about 0.462 g/ml, Crospovidone® having a particle size of about 400 microns and a density of about 1.22 g/ml, and croscarmellose sodium (Ac-Di-Sol) having a particle size of about 37 to about 73.7 microns and a density of about 0.529 g/ml. The disintegrant selected should contribute to the compressibility, flowability and homogeneity of the formulation. Further the disintegrant can minimize segregation and provide an immediate release profile to the formulation. In some embodiments, the disintegrant (s) are present in an amount from about 2 to about 25 percent by weight on a solid basis of the directly compressible formulation. Furthermore, antacids added to the formulations may aid in tablet disintegration when the tablet is introduced to a low pH environment through the effervescence of the antacid ingredient, thus potentially reducing the requirement for additional disintegrants.

In one embodiment, the present invention can include one or more pharmaceutically acceptable glidants, including but not limited to colloidal silicon dioxide. In one embodiment, colloidal silicon dioxide (Cab-O-Sil®) having a density of about 0.029 to about 0.040 g/ml can be used to improve the flow characteristics of the formulation. Such glidants can be provided in an amount of from about 0.1 to about 1 percent by weight of the formulation on a solid basis. It will be understood, based on this invention, however, that while colloidal silicon dioxide is one particular glidant, other glidants having similar properties which are known or to be developed could be used provided they are compatible with other excipients and the active ingredient in the formulation and which do not significantly affect the flowability, homogeneity and compressibility of the formulation.

In one embodiment, the present invention can include one or more pharmaceutically acceptable lubricants, including but not limited to magnesium stearate. In one embodiment, the lubricant, e.g., magnesium stearate, has a particle size of about 450 to about 550 microns and a density of about 1.00 to about 1.80 g/ml. In one embodiment, the lubricant, e.g., magnesium stearate, can contribute to reducing friction between a die wall and a pharmaceutical composition of the present invention during compression and can ease the ejection of the tablets, thereby facilitating processing. In some embodiments, the lubricant resists adhesion to punches and dies and/or aid in the flow of the powder in a hopper and/or into a die. In an embodiment of the present invention, a lubricant, e.g., magnesium stearate, having a particle size of from about 5 to about 50 microns and a density of from about 0.1 to about 1.1 g/ml is used in a pharmaceutical composition. In certain embodiments, a lubricant should make up from about 0.1 to about 2 percent by weight of the formulation on a solids basis. Suitable lubricants are stable and do not polymerize within the formulation once combined. Other lubricants known in the art or to be developed which exhibit acceptable or comparable properties include stearic acid, hydrogenated oils, sodium stearyl fumarate, polyethylene glycols, and Lubritab®.

Dosage Form Functionality

As described herein, pharmaceutical formulations of the present invention may be formulated to slow or block the release and subsequent absorption of excessive doses of an active pharmaceutical ingredient. In some embodiments, a pharmaceutical formulation may be designed with a pH modifying feature and/or a pH dependent solubility feature. A pH modifying feature may impact release and/or absorption of an active ingredient by modifying the pH of the gastric environment based on whether the pharmaceutical composition is taken an appropriate dosage amount or in excess. A pH modifying feature may be provided by inclusion of one or more buffering and/or antacid ingredients in the pharmaceutical composition. A pH dependent solubility feature may impact release and/or absorption of an active ingredient by containing or releasing the active pharmaceutical ingredient, depending on the pH of the gastrointestinal environment. A pH dependent solubility feature may be provided by inclusion of one or more acid soluble ingredients in the pharmaceutical composition.

In some embodiments, the pharmaceutical composition may be formulated such that when the composition is taken in appropriate amounts, a pH modifying feature has minimal impact (i.e., the pH of the gastric environment is not substantially modified or is maintained at a desirable level) and a pH dependent solubility feature has a maximal impact (i.e., the active pharmaceutical ingredient is released), thereby allowing release and/or absorption of the active ingredient. However, when the pharmaceutical composition is ingested in excess, in some embodiments the composition is formulated such that the pH modifying feature has a maximal impact (i.e., the pH of the gastric environment is raised) and the pH dependent solubility feature has a minimal impact (i.e., the acid solubility ingredient is not soluble and therefore does not dissolve), thereby thwarting release and/or absorption of the active ingredient.

The release of the drug from a matrix may then be controlled by the immediate pH environment surrounding the matrix when the pharmaceutical composition is ingested. In a low pH environment (i.e., pH 1-4), the matrix may be likely to dissolve and release the drug rapidly, however, in a higher pH environment (i.e., pH>4) the matrix is likely to be insoluble and the release of drug will be retarded and potentially incomplete, thereby diminishing the level of the drug absorbed.

In some embodiments, for a single dosage unit, the required amount of acid soluble drug matrix is further mixed with buffering and/or antacid ingredient(s) in a quantity sufficient such that when the single dose unit is ingested, the buffering and/or antacid ingredient(s) will neutralize stomach pH to a point that the stomach pH remains in a range between pH 1-4. The acid soluble drug matrix/antacid/buffer blend may be formed into an oral solid dose form such as a tablet or capsule but not limited to said dosage forms.

As a result, a pharmaceutical composition may be formulated having a pH modifying feature and a pH dependent solubility feature such that, under normal dosing conditions, i.e., one or two tablets, when a single dose is ingested, the buffer/antacid ingredient(s) neutralize a portion of the stomach acid, however the stomach acidity remains in a range between pH 1-4. Under these conditions, the acid soluble drug matrix is soluble in the acidic stomach environment and the drug may be rapidly released in the stomach and absorbed into the bloodstream.

Under conditions where excess doses are ingested, e.g., three tablets or greater, the quantity of buffers and/or antacid ingredient(s) from over-ingestion may now be sufficient to cause a rapid and sustainable increase in stomach pH, e.g., pH>4. Thus the acid soluble drug matrix may be less soluble in the higher pH stomach environment and the release of drug from the matrix may be suppressed.

In some embodiments, the suppression of drug from the acid soluble matrix is further aided by gastro-intestinal transit, which may transfer the acid soluble matrix particle into the intestine and lower gastro-intestinal tract which have biologically controlled high pH environments, i.e., pH 5.5-8.

In some embodiments, the overall suppression of drug release from over ingestion results in a pharmacokinetic profile with an increase in $T_{max}$ and/or a decrease in $C_{max}$ when compared to an equal oral dose which releases drug in normal stomach pH, i.e., pH 1-4.

In some embodiments an ingredient that reduces gastric acid production delays the time to stomach re-acidification, thereby prolonging the elevated pH of the gastric environment and enhancing the suppression of active drug release in the event of excess ingestion (i.e., three or more doses or tablets).

In some embodiments an ingredient that reduces gastric acid is not released from the pharmaceutical composition until the pH of the surrounding medium (e.g. gastric environment) is elevated, e.g., above about 4, above about 4.5, above about 5, etc. At such elevated pH a constituent in contact with or coating the ingredient that reduces gastric acid dissolves.

In some embodiments the second buffering ingredient is not released from the delayed release buffering component until the pH of the surrounding medium (e.g. gastric environment) is elevated, e.g., above about 4, above about 4.5, above about 5, etc. At such elevated pH, the enteric agent of the delayed release buffering component dissolves. In some embodiments release of the second buffering component can be further delayed by inclusion of an acid soluble component as previously described herein.

In some embodiments a delayed release buffering component extends the duration of time over which the elevated pH of the gastric environment is maintained, thereby prolonging the suppression of active drug release in the event of excess ingestion (i.e., three or more doses or tablets). In some embodiments, the invention relates to a dosage form that includes an acid soluble ingredient, active pharmaceutical ingredient, first buffering ingredient, an ingredient for decreasing production of gastric acid, and a delayed release buffering component comprising a second buffering ingredient and an enteric agent. In some such embodiments the delayed release buffering component serves to prevent re-acidification for a time sufficient for the ingredient for decreasing production of gastric acid to reach sufficient or maximum plasma levels. For example, in some embodiments the combination of a first buffering ingredient and a delayed release buffering component comprising a second buffering ingredient and an enteric agent prevents re-acidification of the gastric environment for greater than 1 hour, greater than 2 hours, or greater than 3 hours. In some embodiments combination of a first buffering ingredient and a delayed release buffering component comprising a second buffering ingredient and an enteric agent prevents re-acidification of the gastric environment for an extended period longer that the first buffering ingredient alone.

Methods of Making

In some embodiments, a pharmaceutical composition may be prepared by intimately mixing the active pharmaceutical ingredient with an acid soluble ingredient(s) by any suitable process. In one embodiment the process is dry or wet granulation. In some embodiment, a particulate matrix is formed in a particulate or granular form. In another embodiment the process is hot melt extrusion. Without wishing to be bound by theory, it is believed that hot melt extrusion may provide more intimate contact between two or more constituents used in the present invention than mixing or other forms of composite formation.

Compressed tablets including the pharmaceutical compositions of the present invention can be direct compression tablets or non-direct compression tablets. In one embodiment, a dosage form of the present invention can be made by wet granulation, and dry granulation (e.g., slugging or roller compaction). The method of preparation and type of excipients are selected to give the tablet formulation desired physical characteristics that allow for the rapid compression of the tablets. After compression, the tablets must have a number of additional attributes such as appearance, hardness, disintegrating ability, and an acceptable dissolution profile.

In one embodiment, the invention relates to a dosage form comprising an abuse deterrent pharmaceutical composition including a drug susceptible to abuse, an acid soluble ingredient, a buffering ingredient, and an ingredient for increasing gastric emptying time, where the dosage form is a food bar or a beverage. Suitable formulations and dosage forms of the present invention include but are not limited to powders, caplets, pills, suppositories, gels, soft gelatin capsules, capsules and compressed tablets manufactured from a pharmaceutical composition of the present invention. The dosage forms can be any shape, including regular or irregular shape depending upon the needs of the artisan.

Choice of fillers and other excipients typically depend on the chemical and physical properties of the drug, behavior of the mixture during processing, and the properties of the final tablets. Adjustment of such parameters is understood to be within the general understanding of one skilled in the relevant art. Suitable fillers and excipients are described in more detail above.

Methods of making dosage forms, including various controlled release dosage forms, and/or abuse deterrent pharmaceutical compositions, and incorporation of one or more layers, are known in the art and described for example in U.S. Pat. No. 9,522,119, U.S. Patent Application Publications Nos. 2009023288, and 20060210633, and International Patent Application Publications Nos. WO2014059512, WO2016023108, WO2007072495, WO2005101983, WO2003011255, WO2005039481, and WO2006123364, the contents of which are incorporated by reference herein in their entireties.

One or more constituents may be present in a layer or "core-shell" type arrangement as described herein for certain constituents.

In some embodiments, one or more component or particle, granule or layer may be sequestered, as described in U.S. Patent Application Publication No. 20120202839, which is incorporated by reference herein in its entirety. Abuse deterrent pharmaceutical compositions including an immediate release unit dose of a pharmaceutically active ingredient, an acid soluble ingredient, and a buffering ingredient are described in U.S. Pat. No. 9,101,636, which is incorporated by reference herein in its entirety.

The present invention can be used to manufacture immediate release, and controlled drug release formulations. Controlled release formulations can include delayed release, bi-modal and tri-modal release, extended and sustained release oral solid dosage preparations.

Methods of Use

In one embodiment, the invention relates to a method of treating a disease alleviated by a drug susceptible to abuse, including administering to a subject in need thereof an abuse deterrent pharmaceutical composition including a drug susceptible to abuse, an acid soluble ingredient, a buffering ingredient, and an ingredient for increasing gastric emptying time.

In one embodiment, the invention relates to a method of treating a disease alleviated by a drug susceptible to abuse, including administering to a subject in need thereof a dosage form comprising an abuse deterrent pharmaceutical composition including a drug susceptible to abuse, an acid soluble ingredient, a buffering ingredient, and an ingredient for increasing gastric emptying time, where the dosage form is a food bar or a beverage.

In one embodiment, the invention relates to a method of treating a disease alleviated by a drug susceptible to abuse, comprising administering to a subject in need thereof an abuse deterrent pharmaceutical composition comprising a drug susceptible to abuse, an acid soluble ingredient, and a buffering ingredient, and a composition for increasing gastric emptying time, comprising an ingredient for increasing gastric emptying time. In some embodiments, the abuse deterrent pharmaceutical composition is administered before the composition for increasing gastric emptying time, after the composition for increasing gastric emptying time, or simultaneously with the composition for increasing gastric emptying time. In some embodiments, the ingredient for increasing gastric emptying time is a monosaccharide, a disaccharide, an oligosaccharide, a polysaccharide, an amino acid, a peptide, a protein, a fatty acid, a monoglyceride, a diglyceride, or a triglyceride. In some embodiments, the ingredient for increasing gastric emptying time is loperamide, diphenoxylate, atropine, difenoxin, an anticholinergic, an antidepressant, an opioids, an antidiarrheal drug, or a gastroparesis inducing drug.

In one embodiment, the invention relates to a method of treating a disease alleviated by a drug susceptible to abuse, including administering to a subject in need thereof an abuse deterrent pharmaceutical composition comprising a drug susceptible to abuse, an acid soluble ingredient, and a buffering ingredient, and a dosage form including a composition for increasing gastric emptying time including an ingredient for increasing gastric emptying time, wherein the dosage form is a food bar or a beverage.

The methods of use also include methods of deterring the abuse of pharmaceutical compositions including a drug susceptible to abuse, an acid soluble ingredient, a buffering ingredient, and an ingredient for increasing gastric emptying time and/or increasing stomach residence time, the methods including increasing the gastric emptying time and/or increasing stomach residence time in a subject that ingested more dose units of the compositions than recommended or prescribed.

In some embodiments, relative to compositions or dosage forms that do not include features of the present invention, the gastric emptying time can be increased in a subject by about 5 minutes, about 10 minutes, about 15 minutes, about 20 minutes, about 25 minutes, about 30 minutes, about 35 minutes, about 40 minutes, about 45 minutes, about 50 minutes, about 55 minutes, about an hour, about 1.25 hours, about 1.5 hours, about 1.75 hours, about 2 hours, about 2.5 hours, or about 3 hours.

Similarly, relative to compositions or dosage forms that do not include features of the present invention, in some embodiments the gastric emptying time or residence time can be increased by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 110%, about 115%, about 120%, about 125%, about 130%, about 135%, about 140%, about 145%, about 150%, about 175%, or about 200%.

The methods of deterring abuse may also include increasing the gastric residence time of a percentage of a drug ingested, when the drug is part of a composition of the present invention in a subject that ingested more dose units (e.g., 3, 4, 5, 6, 7, 8, and the like, or more) of the compositions than recommended or prescribed.

In some embodiments, relative to compositions or dosage forms that do not include features of the present invention, the gastric residence time can be increased for about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 99.9% of the total amount of drug ingested at a time.

In some embodiments, relative to compositions or dosage forms that do not include features of the present invention, the gastric residence time can be increased for a percentage of the total amount of drug ingested at a time by about 5 minutes, about 10 minutes, about 15 minutes, about 20 minutes, about 25 minutes, about 30 minutes, about 35 minutes, about 40 minutes, about 45 minutes, about 50 minutes, about 55 minutes, about an hour, about 1.25 hours, about 1.5 hours, about 1.75 hours, about 2 hours, about 2.5 hours, or about 3 hours.

In some embodiments, relative to compositions or dosage forms that do not include features of the present invention, the gastric residence time can be increased for a percentage of the total amount of drug ingested at a time by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 110%, about 115%, about 120%, about 125%, about 130%, about 135%, about 140%, about 145%, about 150%, about 175%, or about 200%.

Certain aspects of the present invention may be better understood as illustrated by the following examples, which are meant by way of illustration and not limitation.

EXAMPLES

Example 1: Limitations of Self-Regulated Formulations

For clinical study AP-LTX-400 (study 400), two prototype hydromorphone HCL 2 mg formulations were employed: LTX-04S and LTX-04P, both having the same micro-particle formulation, but differing in the amount of buffer (5 and 9 mEq buffer capacity, respectively). Study 400 was designed for two sequential cohorts. In Cohort 1, both test formulations were compared vs. a reference product, i.e., Dilaudid® tablets, 2 mg, at 1, 2, and 3 tablets. In Cohort 2, the LTX-04P test formulation was tested and compared to the reference product at 4, 6, and 8 tablets, representing excessive oral consumption.

In Cohort 1 it was noticed that the micro-particle did not fully release hydromorphone to the intended levels. It was also observed that for 3 tablets of LTX-04P, an approximate 20% reduction in peak plasma drug levels ($C_{max}$) was achieved compared to a single dose of LTX-04P. It was further observed that 3 tablets of LTX-04P (27 mEq buffer) demonstrated a 28% reduction in peak plasma drug levels ($C_{max}$) compared to 3 tablets of LTX-04S (15 mEq buffer), thus showing that a threshold buffer level had been achieved to facilitate the intended reduction in peak drug levels. In-vivo pH monitoring of subjects demonstrated that 3 LTX-04P tablets resulted in gastric pH rapidly rising above pH 4 within minutes of administration and subsiding after approximately 30 minutes to a baseline low pH, whereas 3 LTX-04S did not rise much above pH 3 over the same time course.

In Cohort 2 of Study 400, LTX-04P tablets were compared to the reference product at 4, 6, and 8 tablets doses. As was the case for 3 LTX-04P tablets in cohort 1, an approximate 20% reduction in peak plasma drug levels were seen for 4, 6, and 8 tablets when compared to a single dose of LTX-04P. These results were unexpected as an in-vitro multi-tablet acid challenge analysis had demonstrated an incremental decrease in drug release with increasing tablet number. For example, 8 tablets resulted in an approximate 70% decrease of in-vitro release after 1 hour, compared to a single tablet drug release of 100% in 1 hr. However, the in-vivo reduction in $C_{max}$ with eight tablets was approximately the same as with 3 tablets, despite introducing 2.7 times more buffering capacity to the gastric environment.

Example 2: Self-Regulated Formulations with Increased Gastric Emptying Time

To demonstrate the synergistic effect of increased gastric emptying time with self-regulating formulations, Study AP-LTX-401 compared the human pharmacokinetics of LTX-04P3, a self-regulated hydromorphone HCl 2 mg formulation, in a model of increased gastric emptying time. A first subject group of 13 was dosed with seven LTX-04P3 tablets with 240 mL of water. A second subject group of 15 was dosed with seven LTX-04P3 tablets with 240 mL of 20% w/v glucose in water, a solution known to increase gastric emptying time. A control group of 30 was administered seven tablets of a generic hydromorphone HCl, 2 mg, with 240 mL of water.

Figure 1:
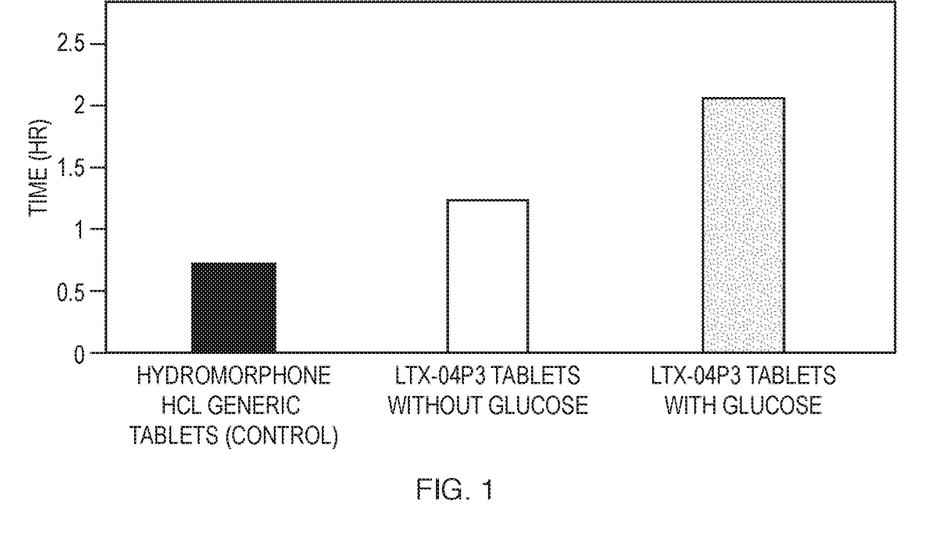
FIG. 1 shows the $T_{max}$ of a formulation according to an embodiment of the invention compared to a control formulation.

The co-administration of glucose with the seven LTX 04P3 demonstrates a significant increase in the geometric mean time to peak plasma hydromorphone concentration ($T_{max}$) of 2.05 hours compared to the $T_{max}$ of LTX-04P3 taken with water of 1.22 hours (FIG. 1). This represents a 168% increase in $T_{max}$ for the glucose treated subjects compared to those without glucose. Glucose delayed gastric emptying (increased gastric retention) which then held the self-regulating buffer ingredient(s) in gastric residence for a longer period of time and enhanced the delay of release of the drug (improved the effectiveness of the self-regulation).

Figure 2:
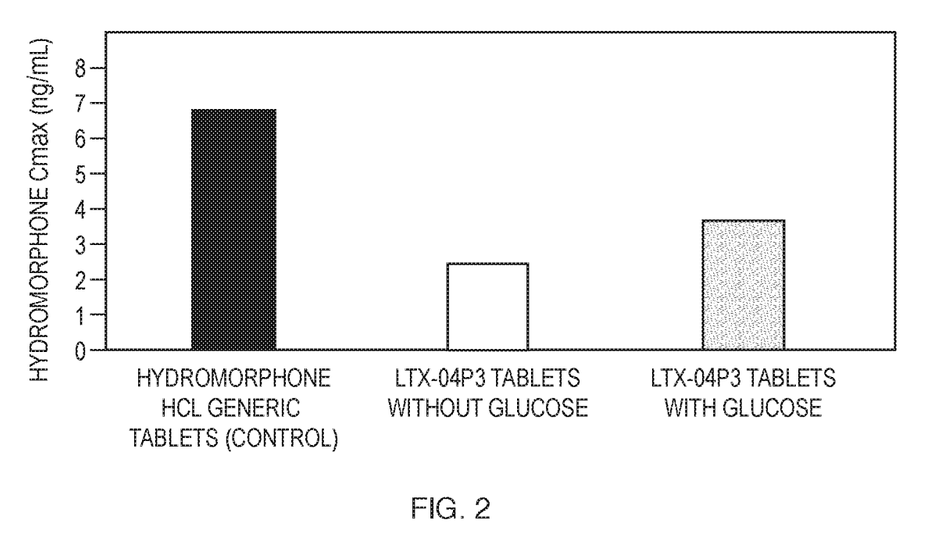
FIG. 2 shows the $C_{max}$ of a formulation according to an embodiment of the invention compared to a control formulation.

The effect of increased gastric retention did not adversely affect the ability of the self-regulating formulation to reduce the geometric mean peak hydromorphone plasma concentration ($C_{max}$). The $C_{max}$ for glucose mediated LTX-04P3 tablets, like that of LTX-04P3 co-administered with water retained its ability to provide a reduction in $C_{max}$ compared to the generic hydromorphone (as shown in FIG. 2).

Example 3: Exemplary Formulations and Processes

An example formulation and process for preparing acid soluble granules is as follows:

Acid Soluble Granules

| Ingredient | Mg/dose | Function |
| --- | --- | --- |
| Oxycodone HCl | 5 | Drug susceptible to abuse |
| Dimethylaminoethyl methacrylate, butyl methacrylate, and methyl methacrylate copolymer (Eudragit E) | 45 | Acid soluble ingredient |
| Total | 50 | |

Process for Preparing Acid Soluble Granules:
1. Uniformly blend Oxycodone and Eudragit E;
2. Hot Melt Extrude blend at 160° C.; collect extruded materials;
3. Size oxycodone-Eudragit E extrudate through an oscillating granulator; collect sieved granules (<600 μm);

An example formulation and process for preparing a delayed release buffering component including a gastric acid reducing agent is as follows:

Delayed release Buffering ingredient with gastric acid reducing agent

| Ingredient | Mg/dose | Function |
| --- | --- | --- |
| Famotidine | 2 | Gastric acid reducing |
| Magnesium oxide | 141 | Second Buffering ingredient |
| Microcrystalline cellulose | 107 | Diluent |
| Dimethylaminoethyl methacrylate, butyl methacrylate, and methyl methacrylate copolymer (Eudragit E PO Ready mix) | 25 | Subcoating A ingredient |
| Hydroxypropyl methylcellulose (Opadry clear) | 10 | Subcoating B ingredient |
| Methyl acrylate-methacrylic acid copolymer (Eudragit L30D) | 29 | Enteric coating ingredient |
| Water | q.s. | Coating solvent |
| Total | 314 | |

Process for Preparing Delayed Release Buffering Ingredient with Gastric Acid Reducing Agent
1. Uniformly blend magnesium oxide and microcrystalline cellulose
2. Roller compact blend and size through an oscillating granulator. Collect sieved dry granules (>250 μm).
3. Prepare Eudragit E PO subcoating A dispersion with a sufficient quantity of water and maintain constant mixing.
4. Prepare Opadry clear/Famotidine subcoating B solution by first mixing the Opadry Clear with a sufficient quantity of water. Next, add and uniformly disperse famotidine into subcoating B and maintain constant mixing.
5. Prepare Eudragit L 30D enteric coating dispersion with a sufficient quantity of water and maintain constant mixing.
6. Place dry granules into fluid bed coater and apply approximately 10% Eudragit E PO subcoating A to the buffer granules by bottom spray processing. After application, allow Eudragit E PO subcoating A to sufficiently dry. Next, in the same fluid bed process, apply enough Opadry Clear/Famotidine subcoating B solution to provide 2 mg Famotidine per dose. After application, allow Opadry Clear/Famotidine subcoating B to sufficiently dry. Next, in the same fluid bed process, apply approximately 10% (w/w) Eudragit L 30% dispersion to subcoated A & B granules and dry to completion.
7. Collect sieved enteric coated delayed release buffer/gastric acid reducing granules (>250 μm)

An example formulation and process for preparing Oxycodone Self-regulating Tablet is as follows:

Oxycodone Self-Regulating Tablet

| Ingredient | Mg/dose | Function |
| --- | --- | --- |
| Oxycodone acid soluble granules | 50 | |
| Sodium Bicarbonate (Effersoda 12) | 235 | First buffer Ingredient |
| Enteric coated Magnesium Oxide/Famotidine Granules | 314 | Second Buffer Ingredient (with gastric acid reducing agent) |
| Glycine | 186 | Gastric Retention ingredient |
| Crospovidone | 37.5 | Disintegrant |
| Magnesium Stearate | 2.5 | Lubricant |
| Total | 825 | |

Process for Preparing Oxycodone Self-Regulating Tablet
1. Uniformly blend Oxycodone acid soluble granules, Effersoda 12, Enteric coated Magnesium Oxide/Famotidine Granules, glycine and crospovidone
2. Add magnesium stearate to the blend and final blend for an additional 3 minutes.
3. Transfer final blend to a rotary tablet press with modified oval tablet tooling. Compress tablets to a hardness of 8-12 kP.

It will be appreciated by persons skilled in the art that numerous variations and/or modifications may be made to the invention shown in the specific embodiments without departing from the spirit and scope of the invention as broadly described. Further, each and every reference cited above is hereby incorporated by reference as if fully set forth herein.

The invention claimed is:
1. An abuse deterrent pharmaceutical composition comprising:
   a drug susceptible to abuse;
   a first acid soluble ingredient;
   a first buffering ingredient;
   an ingredient for increasing gastric emptying time; and
   a delayed release buffering component, wherein the delayed release buffering component comprises:
   a core comprising a second buffering ingredient,
   a core coating comprising a sustained-release ingredient,
   a shell comprising an enteric ingredient, and
   a subcoat between the core coating and the shell, wherein the subcoat comprises an ingredient for decreasing gastric acid production, and
   the ingredient for increasing gastric emptying time is selected from the group consisting of a monosaccharide, a disaccharide, an oligosaccharide, an amino acid, a peptide, a protein, a monoglyceride, a diglyceride, and a triglyceride.
2. The composition of claim 1, wherein the first acid soluble ingredient comprises calcium carbonate, a cationic copolymer, or a combination thereof.
3. The composition of claim 2, wherein the cationic copolymer comprises one or more of dimethylaminoethyl methacrylate, butyl methacrylate, or methyl methacrylate.

4. The composition of claim 1, wherein the first buffering ingredient comprises calcium carbonate, sodium bicarbonate, magnesium oxide, tribasic sodium phosphate, or combinations thereof.

5. The composition of claim 1, wherein the delayed release buffering component further comprises a second acid-soluble ingredient.

6. The composition of claim 5, wherein the subcoat comprises the second acid-soluble ingredient.

7. The composition of claim 6, wherein the second acid soluble ingredient comprises calcium carbonate, a cationic copolymer, or combinations thereof.

8. The composition of claim 7, wherein the cationic copolymer comprises one or more of dimethylaminoethyl methacrylate, butyl methacrylate, or methyl methacrylate.

9. The composition of claim 5 wherein the second acid soluble ingredient is the same as the first acid soluble ingredient.

10. The composition of claim 1, wherein the second buffering ingredient comprises calcium carbonate, sodium bicarbonate, magnesium oxide, tribasic sodium phosphate, or combinations thereof.

11. The composition of claim 1, wherein the second buffering ingredient is the same as the first buffering ingredient.

12. The composition of claim 1, wherein the enteric ingredient comprises one or more of shellac, methyl acrylate-methacrylic acid copolymers, cellulose acetate phthalate, cellulose acetate succinate, hydroxypropyl methyl cellulose phthalate, hypromellose acetate succinate, polyvinyl acetate phthalate, sodium alginate, or zein.

13. The composition of claim 1, wherein the ingredient for decreasing gastric acid production comprises an H2-antagonist.

14. The composition of claim 13, wherein the H2-antagonist is present in an amount that is 10-50% of the lowest therapeutic dose of the H2 antagonist for reducing stomach acid secretion.

15. The composition of claim 1, wherein upon ingestion by a subject, the ingredient for increasing gastric emptying time increases the gastric emptying time of the subject.

16. A dosage form comprising the composition of claim 1.

17. The dosage form of claim 16, wherein the dosage form is a food bar or a beverage.

18. A method of treating a disease alleviated by a drug susceptible to abuse, comprising:
   administering to a subject in need thereof a composition of claim 1.

* * * * *